United States Patent [19]

Schutt et al.

[11] Patent Number: 5,605,673
[45] Date of Patent: Feb. 25, 1997

[54] STABILIZED MICROBUBBLE COMPOSITIONS FOR ULTRASOUND

[75] Inventors: Ernest G. Schutt, San Diego; Charles D. Anderson, Lebanon; David P. Evitts, La Jolla, all of Calif.

[73] Assignee: Alliance Pharmaceutical Corp., San Diego, Calif.

[21] Appl. No.: 284,083

[22] Filed: Aug. 1, 1994

Related U.S. Application Data

[63] Continuation-in-part of Ser. No. 99,951, Jul. 30, 1993, abandoned.

[51] Int. Cl.⁶ ................................................. A61K 49/00
[52] U.S. Cl. ................................................. 424/9.51
[58] Field of Search ........................ 424/9.5, 9.51, 424/9.52

[56] References Cited

U.S. PATENT DOCUMENTS

| | | | |
|---|---|---|---|
| 4,681,119 | 7/1987 | Rasor et al. | 424/9.52 |
| 4,844,882 | 7/1989 | Widder et al. | 424/9 |
| 5,186,922 | 2/1993 | Shell et al. | 128/654 |
| 5,271,928 | 12/1993 | Schneider et al. | 424/9 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,333,613 | 8/1994 | Tickner et al. | 128/662.02 |
| 5,334,381 | 8/1994 | Unger | 424/9 |
| 5,348,016 | 9/1994 | Unger et al. | 128/662.02 |
| 5,352,435 | 10/1994 | Unger | 424/9 |
| 5,352,436 | 10/1994 | Wheatley et al. | 424/9 |
| 5,376,380 | 12/1994 | Kikuchi et al. | 424/450 |
| 5,380,519 | 1/1995 | Schneider et al. | 424/9 |
| 5,393,524 | 2/1995 | Quay | 424/9 |
| 5,558,856 | 9/1996 | Klaveness et al. | 424/9.37 |
| 5,558,857 | 9/1996 | Klaveness et al. | 424/9.52 |

FOREIGN PATENT DOCUMENTS

| | | |
|---|---|---|
| 6528038 | 9/1994 | Australia. |
| 0131540A2 | 1/1985 | European Pat. Off. |
| 0586875A1 | 2/1989 | European Pat. Off. |
| 0320433A3 | 6/1989 | European Pat. Off. |
| 0606613A1 | 7/1994 | European Pat. Off. |
| 8905160 | 6/1989 | WIPO. |
| 8906978 | 8/1989 | WIPO. |
| 9211873 | 7/1992 | WIPO. |
| 9222249 | 12/1992 | WIPO. |
| 9303671 | 3/1993 | WIPO. |
| 9325242 | 12/1993 | WIPO. |
| 9401140 | 1/1994 | WIPO. |
| 9406477 | 3/1994 | WIPO. |
| 9409703 | 5/1994 | WIPO. |
| 9408707 | 4/1994 | WIPO. |
| 9409829 | 5/1994 | WIPO. |
| 9416739 | 8/1994 | WIPO. |
| 9421175 | 9/1994 | WIPO. |
| 0458745B1 | 9/1994 | WIPO. |
| 9428939 | 12/1994 | WIPO. |
| 9428797 | 12/1994 | WIPO. |
| 9628090 | 9/1996 | WIPO. |

OTHER PUBLICATIONS

Kitagawa, et al. *Biological Abstracts* 63:6392 (1977).
Keough, et al. *Biological Abstracts* 105308 (1986).
Matsuda, et al. "Contrast Echocardiography of the Left Heart by Intravenous Injection of Perfluorochemical Emulsion" *J. of Cardiography* 13(4): 1021–1028 (1983).
Sunamoto, et al. "Liposomal Membranes" *J. Biochem.* 88:1219–1226 (1980).
N. de Jong, et al. "Principles and Recent Developments in Ultrasound Contrast Agents", *Ultrasonics*. 29:324–330, 1991.

*Primary Examiner*—Brian M. Burn
*Assistant Examiner*—Mary C. Cebulak
*Attorney, Agent, or Firm*—Knobbe, Martens Olson & Bear

[57] ABSTRACT

A microbubble preparation formed of a plurality of microbubbles comprising a first gas and a second gas surrounded by a membrane such as a surfactant, wherein the first gas and the second gas are present in a molar ratio of from about 1:100 to about 1000:1, and wherein the first gas has a vapor pressure of at least about (760−x) mm Hg at 37° C., where x is the vapor pressure of the second gas at 37° C., and wherein the vapor pressure of each of the first and second gases is greater than about 75 mm Hg at 37° C.; also disclosed are methods for preparing microbubble compositions, including compositions that rapidly shrink from a first average diameter to a second average diameter less than about 75% of the first average diameter and are stabilized at the second average diameter; methods and kits for preparing microbubbles; and methods for using such microbubbles as contrast agents.

82 Claims, 2 Drawing Sheets

STABILIZED MICROBUBBLE COMPOSITIONS FOR ULTRASOUND

CROSS REFERENCE TO RELATED APPLICATIONS

This is a continuation-in-part of U.S. application Ser. No. 08/099,951, filed Jul. 30, 1993, now abandoned.

BACKGROUND OF THE INVENTION

1. Field of the Invention

The present invention includes a method for preparing stable long-lived microbubbles for ultrasound contrast enhancement and other uses, and to compositions of the bubbles so prepared.

2. Background of the Art

Ultrasound technology provides an important and more economical alternative to imaging techniques which use ionizing radiation. While numerous conventional imaging technologies are available, e.g., magnetic resonance imaging (MRI), computerized tomography (CT), and positron emission tomography (PET), each of these techniques use extremely expensive equipment. Moreover, CT and PET utilize ionizing radiation. Unlike these techniques, ultrasound imaging equipment is relatively inexpensive. Moreover, ultrasound imaging does not use ionizing radiation.

Ultrasound imaging makes use of differences in tissue density and composition that affect the reflection of sound waves by those tissues. Images are especially sharp where there are distinct variations in tissue density or compressibility, such as at tissue interfaces. Interfaces between solid tissues, the skeletal system, and various organs and/or tumors are readily imaged with ultrasound.

Accordingly, in many imaging applications ultrasound performs suitably without use of contrast enhancement agents; however, for other applications, such as visualization of flowing blood, there have been ongoing efforts to develop such agents to provide contrast enhancement. One particularly significant application for such contrast agents is in the area of perfusion imaging. Such ultrasound contrast agents could improve imaging of flowing blood in the heart muscle, kidneys, liver, and other tissues. This, in turn, would facilitate research, diagnosis, surgery, and therapy related to the imaged tissues. A blood pool contrast agent would also allow imaging on the basis of blood content (e.g., tumors and inflamed tissues) and would aid in the visualization of the placenta and fetus by enhancing only the maternal circulation.

A variety of ultrasound contrast enhancement agents have been proposed. The most successful agents have generally consisted of microbubbles that can be injected intravenously. In their simplest embodiment, microbubbles are miniature bubbles containing a gas, such as air, and are formed through the use of foaming agents, surfactants, or encapsulating agents. The microbubbles then provide a physical object in the flowing blood that is of a different density and a much higher compressibility than the surrounding fluid tissue and blood. As a result, these microbubbles can easily be imaged with ultrasound.

Most microbubble compositions have failed, however, to provide contrast enhancement that lasts even a few seconds, let alone minutes, of contrast enhancement. This greatly limits their usefulness. Microbubbles have therefore been "constructed" in various manners in an attempt to increase their effective contrast enhancement life. Various avenues have been pursued: use of different surfactants or foaming agents; use of gelatins or albumin microspheres that are initially formed in liquid suspension, and which entrap gas during solidification; and liposome formation. Each of these attempts, in theory, should act to create stronger bubble structures. However, the entrapped gases (typically air, $CO_2$, and the like) are under increased pressure in the bubble due to the surface tension of the surrounding surfactant, as described by the Laplace equation ($\Delta P = 2\gamma/r$).

This increased pressure, in turn, results in rapid shrinkage and disappearance of the bubble as the gas moves from a high pressure area (in the bubble) to a lower pressure environment (in either the surrounding liquid which is not saturated with gas at this elevated pressure, or into a larger diameter, lower pressure bubble).

Solid phase shells that encapsulate gases have generally proven too fragile or too permeable to the gas to have satisfactory in vivo life. Furthermore, thick shells (e.g., albumin, sugar, or other viscous materials) reduce the compressibility of the bubbles, thereby reducing their echogenicity during the short time they can exist. Solid particles or liquid emulsion droplets that evolve gas or boil when injected pose the danger of supersaturating the blood with the gas or vapor. This will lead to a small number of large embolizing bubbles forming at the few available nucleation sites rather than the intended large number of small bubbles.

One proposal for dealing with such problems is outlined in Quay, PCT/US92/07250. Quay forms bubbles using gases selected on the basis of being a gas at body temperature (37° C.) and having reduced water solubility, higher density, and reduced gas diffusivity in solution in comparison to air. Although reduced water solubility and diffusivity can affect the rate at which the gas leaves the bubble, numerous problems remain with the Quay bubbles. Forming bubbles of sufficiently small diameter (e.g., 3–5 μm) requires high energy input. This is a disadvantage in that sophisticated bubble preparation systems must be provided at the site of use. Moreover, The Quay gas selection criteria are incorrect in that they fail to consider certain major causes of bubble shrinkage, namely, the effects of bubble surface tension, surfactants and gas osmotic effects, and these errors result in the inclusion of certain unsuitable gases and the exclusion of certain optimally suitable gases.

Accordingly, a need exists in the art for compositions, and a method to prepare such compositions, that provide, or utilize, a longer life contrast enhancement agent that is biocompatible, easily prepared, and provides superior contrast enhancement in ultrasound imaging.

SUMMARY OF THE INVENTION

In accordance with the present invention, there is provided an ultrasound contrast enhancement agent that has a prolonged longevity in vivo, which consists of virtually any conventional microbubble formulation in conjunction with an entrapped gas or gas mixture that is selected based upon consideration of partial pressures of gases both inside and outside of the bubble, and on the resulting differences in gas osmotic pressure that oppose bubble shrinkage. Gases having a low vapor pressure and limited solubility in blood or serum (i.e., relatively hydrophobic) may advantageously be provided in combination with another gas that is more rapidly exchanged with gases present in normal blood or serum. Surfactant families allowing the use of higher molecular weight gas osmotic agents, and improved methods of bubble production are also disclosed.

One aspect of the present invention is a stabilized gas filled microbubble preparation, comprising a mixture of a first gas or gases and a second gas or gases (gas osmotic agent) within generally spherical membranes to form microbubbles, wherein the first gas and the second gas are respectively present in a molar ratio of about 1:100 to about 1000:1, and wherein the first gas has a vapor pressure of at least about (760–x) mm Hg at 37° C., where x is the vapor pressure of the second gas at 37° C., and wherein the vapor pressure of each of the first and second gases is greater than about 75 mm Hg at 37° C., with the proviso that the first gas and the second gas are not water vapor. In one embodiment, the second gas comprises a fluorocarbon and the first gas is a nonfluorocarbon, such as nitrogen, oxygen, carbon dioxide, or a mixture thereof.

The microbubbles may advantageously be provided in a liquid medium, such as an aqueous medium, wherein they have a first average diameter, the ratio of the first gas to the second gas in the microbubbles is at least 1:1, and the microbubbles are adapted to shrink in the medium as a result of loss of the first gas through the membrane to a second average diameter of less than about 75% of the first diameter and then remain stabilized at or about the second diameter for at least about 1 minute as a result of a gas osmotic pressure differential across the membrane. Advantageously, the medium is in a container and the microbubbles have actually been formed in the container. Alternatively, the medium is blood in vivo. In one embodiment, the liquid medium contains gas or gases dissolved therein with a gas tension of at least about 700 mm Hg, wherein the first diameter is at least about 5 µm, and wherein the tension of the gas or gases dissolved in the medium is less than the partial pressure of the same gas or gases inside the microbubbles.

In a particularly preferred embodiment, the bubble initially contains at least three gases: a first gas having a partial pressure far greater than the gas tension of the same gas in the surrounding liquid (e.g., 1.5, 2, 4, 5, 10, 20, 50, or 100 or more times greater than in the surrounding liquid); a second gas that is retained in the bubble due to a relatively low permeability of the bubble membrane to the gas, or a relatively low solubility of the gas in the surrounding medium (as described elsewhere herein), and a third gas to which the membrane is relatively permeable that is also present in the surrounding medium. For example, in an aqueous system exposed to or at least partially equilibrated with air (such as blood), the first gas may advantageously be carbon dioxide or another gas not present in large quantities in air or blood; the second gas may be a fluorocarbon gas, such as perfluorohexane; and the third gas may be air or a major component of air such as nitrogen or oxygen.

Preferably, the first diameter prior to shrinkage is at least about 10 µm and the second diameter at which the diameter is stabilized is between about 1 µm and 6 µm.

For all of the microbubble preparations or methods described herein, in one preferred embodiment, the second gas has an average molecular weight at least about 4 times that of the first gas. In another preferred embodiment, the second gas has a vapor pressure less than about 750 or 760 mm Hg at 37° C. Moreover, it is preferred that the molar ratio of the first gas to the second gas is from about 1:10 to about 500:1, 200:1, or 100:1. In other preferred embodiments, the second gas comprises a fluorocarbon or a mixture of at least two or three fluorocarbons, and the first gas is a nonfluorocarbon. In some advantageous preparations, the second gas comprises one or more perfluorocarbons. In others, both the first gas and the second gas comprise fluorocarbons. In still others, the microbubbles contain as the first gas, or as the second gas, or respectively as the first and second gases, gaseous perfluorobutane and perfluorohexane in a ratio from about 1:10 to about 10:1. Alternatively, the microbubbles contain as the first gas, or as the second gas, or respectively as the first and second gases, gaseous perfluorobutane and perfluoropentane in a ratio from about 1:10 to about 10:1. It is advantageous that the second gas leave the microbubble much more slowly than does the first gas; thus, it is preferred that the second gas has a water solubility of not more than about 0.5 mM at 25° C. and one atmosphere, and the first gas has a water solubility at least about 10 times, and preferably at least 20, 50, 100, or 200 times greater than that of the second gas. Similarly, it is preferred that the permeability of the membrane to the first gas is at least about 5 times, preferably 10, 20, 50, or 100 times greater than the permeability of the membrane to the second gas.

The microbubble preparation may advantageously be contained in a container, having a liquid in the container in admixture with the microbubbles, wherein the container further comprises means for transmission of sufficient ultrasonic energy to the liquid to permit formation of the microbubbles by sonication. In this way, the microbubbles can be formed by the physician (or other professional) immediately before use by applying ultrasonic energy from an outside source to the sterile preparation inside the container. This means for transmission can, for example, be a flexible polymer material having a thickness less than about 0.5 mm (which permits ready transmission of ultrasonic energy without overheating the membrane). Such membranes can be prepared from such polymers as natural or synthetic rubber or other elastomer, polytetrafluoroethylene, polyethylene terephthalate, and the like.

In the microbubble preparations of the invention, the membrane enclosing the gas is preferably a surfactant. One preferred type of surfactant comprises a non-Newtonian viscoelastic surfactant, alone or in combination with another surfactant. Other preferred general and specific categories of surfactants include carbohydrates, such as polysaccharides, derivatized carbohydrates, such as fatty acid esters of sugars such as sucrose (preferably sucrose stearate), and proteinaceous surfactants including albumin. Alternatively, the membrane of the microbubble need not be a fluid (such as a surfactant), but instead can be a solid or semi-solid, such as hardened, thickened, or denatured proteinaceous material (e.g. albumin), carbohydrates, and the like.

One advantageous form of the invention is a kit for use in preparing microbubbles, preferably at the site of use. This kit may comprise sealed container (such as a vial with a septum seal for easy removal of the microbubbles using a hypodermic syringe), a liquid in the container (such as water or a buffered, isotonic, sterile aqueous medium), a surfactant in the container, and a fluorocarbon gas (including a fluorocarbon vapor) in the container, wherein the liquid, the surfactant, and the fluorocarbon gas or vapor are together adapted to form microbubbles upon the application of energy thereto. The energy advantageously may be simple shaking energy, either manual or mechanical, stirring or whipping, or ultrasonic energy. The kit preferably includes means in the container for permitting transmission of sufficient external ultrasonic energy to the liquid to form microbubbles in the container. As above, the means for transmission can in one embodiment comprise a flexible polymer membrane having a thickness less than about 0.5 mm. In one embodiment, the kit further includes a nonfluorocarbon gas in the container, wherein the molar ratio of the nonfluorocarbon gas to the fluorocarbon gas is from about 1:10 to about 1000:1, with the proviso that the nonfluorocarbon gas is not water vapor. In all of the kits of the present invention, the surfactant, the gas or gases, and the other elements of the kit may in some embodiments be the same as recited above for the microbubble preparation per se.

In another embodiment, the kit comprises a container, dried liquid-soluble void-containing structures in the container, the void-containing structures defining a plurality of voids having an average diameter less than about 100 μm, a gas in the voids, and a surfactant, wherein the void-containing structures, the gas, and the surfactant are together adapted to form microbubbles upon addition to the container of a liquid in which the void-containing structures are soluble. These void-containing structures can be made at least in part of the surfactant, e.g., by lyophilization of void-forming material or by spray drying, or can be formed from any other liquid soluble (preferably water soluble) film-forming material, such as albumin, enzymes, or other proteins, simple or complex carbohydrates or polysaccharides, and the like. The surfactants used in the kit can advantageously be those described above in connection with the microbubble preparations per se.

The present invention also includes a method for forming microbubbles, comprising the steps of providing a first gas, a second gas, a membrane forming material, and a liquid, wherein the first gas and the second gas are present in a molar ratio of from about 1:100 to about 1,000:1, and wherein the first gas has a vapor pressure of at least about (760−x) mm Hg at 37° C., where x is the vapor pressure of the second gas at 37° C., and wherein the vapor pressure of each of the first and second gases is greater than about 75 mm Hg at 37° C., with the proviso that the first gas and the second gas are not water vapor, and surrounding the first and second gases with the membrane forming material to form microbubbles in the liquid. The membrane forming materials and gases may be as described above. The method preferably further comprises the steps of initially forming microbubbles having a first average diameter wherein the initial ratio of the first gas to the second gas in the microbubbles is at least about 1:1, contacting the microbubbles having a first average diameter with a liquid medium, shrinking the microbubbles in the medium as a result of loss of the first gas through the membrane, and then stabilizing the microbubbles at a second average diameter of less than about 75% of the first diameter for a period of at least one minute. Preferably, the microbubbles are stabilized at the second diameter by providing a gas osmotic pressure differential across the membrane such that the tension of a gas or gases dissolved in the medium is greater than or equal to the pressure of the same gas or gases inside the microbubbles. In one embodiment, the first diameter is at least about 5 μm.

The invention also includes a method for forming microbubbles, comprising the steps of providing dried liquid-soluble void-containing structures, the void-containing structures defining a plurality of voids having a diameter less than about 100 μm, providing a gas in the voids, providing a surfactant, combining together the void-containing structures, the gas, the surfactant, and a liquid in which the void-containing structures are soluble, and dissolving the void-containing structures in the liquid whereby the gas in the enclosures forms microbubbles that are surrounded by the surfactant. As with the kit, preferred void-containing structures are formed of protein, surfactant, carbohydrate, or any of the other materials described above.

Another aspect of the present invention is a method for producing microbubbles having increased in-vial stability, comprising the steps of spray drying a liquid formulation of a biocompatible material to produce hollow microspheres therefrom, permeating the microspheres with a gas osmotic agent (the second gas) mixed with the first gas and storing the microspheres in a container with the gas mixture, and then adding an aqueous phase to the powder, wherein the powder dissolves in the aqueous phase to entrap the gas mixture within a liquid surfactant membrane to form microbubbles. In one embodiment, the microsphere comprises a starch or starch derivative having a molecular weight of greater than about 500,000 or a dextrose equivalency value less than about 12. One preferred starch derivative is hydroxyethyl starch. Preferably, the gas osmotic agent comprises a perfluorocarbon. In another embodiment, the microsphere comprises a sugar ester having a component with a hydrophilic-lipophilic balance less than about eight. Preferably, the sugar ester is sucrose tristearate.

The present invention also includes a method for forming microbubbles, comprising the step of providing a gas osmotic agent-permeated surfactant powder, and combining the powder with an aqueous phase.

Still another aspect of the present invention is a method for increasing the in vivo half-life of microbubbles, comprising providing a spray dried formulation in combination with a gas osmotic agent that permeates the formulation, and combining the formulation with an aqueous phase to form microbubbles having a half-life in vivo of at least about 20 seconds. In preferred embodiments, the spray dried formulation comprises a starch or starch derivative and the sugar ester is sucrose tristearate.

Finally, the present invention includes a method for imaging an object or body, comprising the steps of introducing into the object or body any of the aforementioned microbubble preparations and then imaging at least a portion of the object or body via ultrasound or magnetic resonance. Preferably, the body is a vertebrate and the preparation is introduced into the vasculature of the vertebrate. The method may further include preparing the microbubbles in any of the aforementioned manners prior to introduction into the animal.

DETAILED DESCRIPTION OF THE INVENTION

Figure 1:
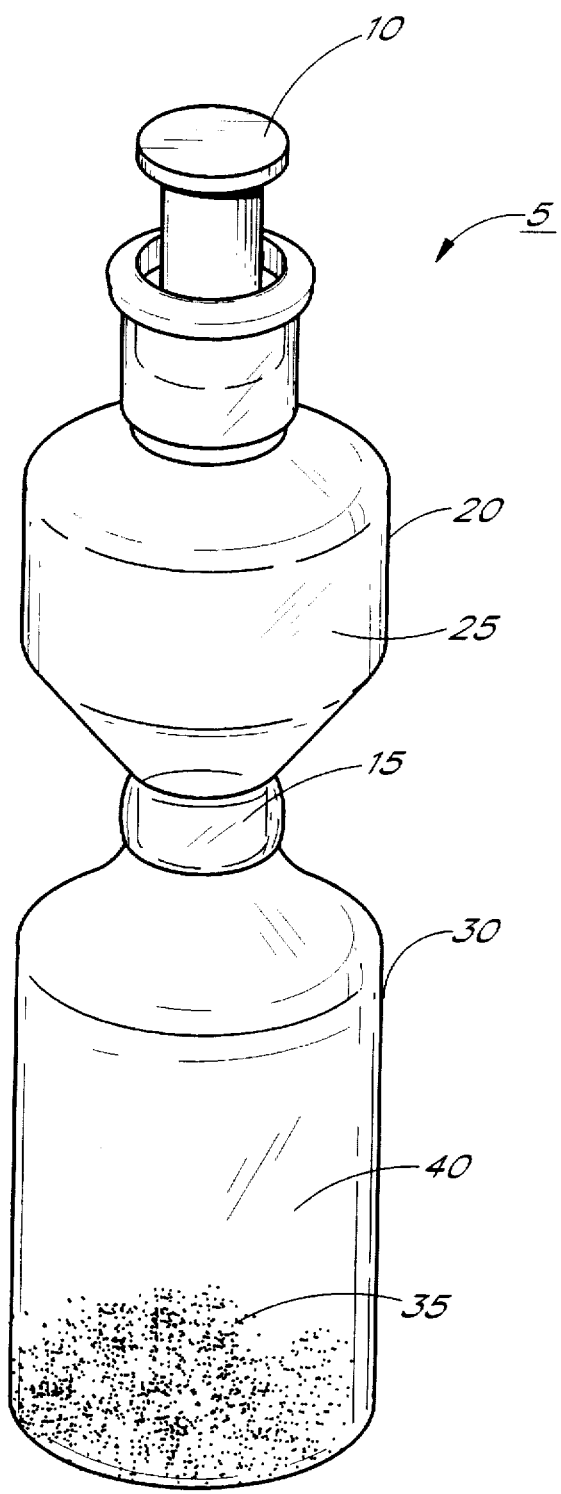
FIG. 1 is a perspective view of a two chamber vial containing a microbubble-forming preparation, with an aqueous solution in an upper chamber and solid and gaseous ingredients in a lower chamber.

As used in the present description and claims, the terms "vapor" and "gas" are used interchangeably. Similarly, when referring to the tension of dissolved gas in a liquid, the more familiar term "pressure" may be used interchangeably with "tension." "Gas osmotic pressure" is more fully defined below, but in a simple approximation can be thought of as the difference between the partial pressure of a gas inside a microbubble and the pressure or tension of that gas (either in a gas phase or dissolved in a liquid phase) outside of the microbubble, when the microbubble membrane is permeable to the gas. More precisely, it relates to differences in gas diffusion rates across a membrane. The term "membrane" is used to refer to the material surrounding or defining a microbubble, whether it be a surfactant, another film forming liquid, or a film forming solid or semisolid. "Microbubbles" are considered to be bubbles having a diameter between about 0.5 and 300 µm, preferably having a diameter no more than about 200, 100, or 50 µm, and for intravascular use, preferably not more than about 10, 8, 7, 6, or 5 µm (measured as average number weighted diameter of the microbubble composition). When referring to a "gas," it will be understood that mixtures of gases together having the requisite property fall within the definition, except where the context otherwise requires. Thus, air may typically be considered a "gas" herein.

The present invention provides microbubbles that have a prolonged longevity in vivo that are suitable for use as ultrasound and magnetic resonance imaging (MRI) contrast enhancement agents. Typical ultrasound contrast enhancement agents exhibit contrast enhancement potential for only about one pass through the arterial system, or a few seconds to about a minute, and thus do not survive past the aorta in a patient following intravenous injection. In comparison, contrast agents prepared in accordance with the present invention continue to demonstrate contrast enhancements lives measured in multiple passes through the entire circulatory system of a patient following intravenous injection. Bubble lives of several minutes are easily demonstrated. Such lengthening of contrast enhancement potential during ultrasound is highly advantageous. In addition, the contrast enhancement agents of the invention provide superior imaging; for example, clear, vivid, and distinct images of blood flowing through the heart, liver, and kidneys are achieved. Thus small, nontoxic doses can be administered in a peripheral vein and used to enhance images of the entire body.

As disclosed in U.S. Pat. No. 5,315,997, gases and perfluorocarbon vapors have magnetic susceptibilities substantially different from tissues and blood. Therefore, the microbubbles of the present invention will cause changes in the local magnetic fields present in tissues and blood during MRI. These changes can be discerned on an MRI image and can be used to detect the presence of a contrast agent. The agent of the invention will persist in the blood pool longer and will therefore allow longer, more sensitive scans of larger portions of the body.

While bubbles have been shown to be the most efficient ultrasound scatterers for use in intravenous ultrasound contrast agents, their main practical drawback is the extremely short lifetime of the small (typically less than 5 microns diameter) bubbles required to pass through capillaries in suspension. This short lifetime is caused by the increased gas pressure inside the bubble, which results from the surface tension forces acting on the bubble. This elevated internal pressure increases as the diameter of the bubble is reduced. The increased internal gas pressure forces the gas inside the bubble to dissolve, resulting in bubble collapse as the gas is forced into solution. The Laplace equation, $\Delta P = 2\gamma/r$, (where $\Delta P$ is the increased gas pressure inside the bubble, $\gamma$ is the surface tension of the bubble film, and r is the radius of the bubble) describes the pressure exerted on a gas bubble by the surrounding bubble surface or film. The Laplace pressure is inversely proportional to the bubble radius; thus, as the bubble shrinks, the Laplace pressure increases, increasing the rate of diffusion of gas out of the bubble and the rate of bubble shrinkage.

It was surprisingly discovered that gases and gas vapor mixtures which can exert a gas osmotic pressure opposing the Laplace pressure can greatly retard the collapse of these small diameter bubbles. In general, the invention uses a primary modifier gas or mixture of gases that dilute a gas osmotic agent to a partial pressure less than the gas osmotic agent's vapor pressure until the modifier gas will exchange with gases normally present in the external medium. The gas osmotic agent or agents are generally relatively hydrophobic and relatively bubble membrane impermeable and also further possess the ability to develop gas osmotic pressures greater than 75 or 100 Torr at a relatively low vapor pressure.

The process of the invention is related to the well known osmotic effect observed in a dialysis bag containing a solute that is substantially membrane impermeable (e.g. PEG, albumin, polysaccharide, starch) dissolved in an aqueous solution is exposed to a pure water external phase. The solute inside the bag dilutes the water inside the bag and thus reduces the rate of water diffusion out of the bag relative to the rate of pure water (full concentration) diffusion into the bag. The bag will expand in volume until an equilibrium is established with an elevated internal pressure within the bag which increases the outward diffusional flux rate of water to balance the inward flux rate of the pure water. This pressure difference is the osmotic pressure between the solutions.

In the above system, the internal pressure will slowly drop as the solute slowly diffuses out of the bag, thus reducing the internal solute concentration. Other materials dissolved in the solution surrounding the bag will reduce this pressure further, and, if they are more effective or at a higher concentration, will shrink the bag.

It was observed that bubbles of air saturated with selected perfluorocarbons grow rather than shrink when exposed to air dissolved in a liquid due to the gas osmotic pressure exerted by the perfluorocarbon vapor. The perfluorocarbon vapor is relatively impermeable to the bubble film and thus remains inside the bubble. The air inside the bubble is diluted by the perfluorocarbon, which acts to slow the air diffusion flux out of the bubble. This gas osmotic pressure is proportional to the concentration gradient of the perfluorocarbon vapor across the bubble film, the concentration of air surrounding the bubble, and the ratio of the bubble film permeability to air and to perfluorocarbon.

As discussed above, the Laplace pressure is inversely proportional to the bubble radius; thus, as the bubble shrinks, the Laplace pressure increases, increasing the rate of diffusion of gas out of the bubble and the rate of bubble shrinkage, and in some cases leading to the condensation and virtual disappearance of a gas in the bubble as the combined Laplace and external pressures concentrate the osmotic agent until its partial pressure reaches the vapor pressure of liquid osmotic agent.

We have discovered that conventional microbubbles that contain any single gas will subsist in the blood for a length of time that depends primarily on the arterial pressure, the bubble diameter, the membrane permeability of the gas through the bubble's surface, the mechanical strength of the bubble's surface, the presence, absence, and concentration of the gases that are ordinarily present in the blood or serum, and the surface tension present at the surface of the bubble (which is primarily dependent on the diameter of the bubble and secondarily dependent on the identity and concentration of the surfactants which form the bubble's surface). Each of these parameters are interrelated, and they interact in the bubble to determine the length of time that the bubble will last in the blood.

The present invention includes the discovery that a single gas or a combination of gases can together act to stabilize the structure of the microbubbles entraining or entrapping them. Essentially, the invention utilizes a first gas or gases (a "primary modifier gas") that optionally is ordinarily present in normal blood and serum in combination with one or more additional second gases (a "gas osmotic agent or agents" or a "secondary gas") that act to regulate the osmotic pressure within the bubble. Through regulating the osmotic pressure of the bubble, the gas osmotic agent (defined herein as a single or mixture of chemical entities) exerts pressure within the bubble, aiding in preventing deflation. Optionally, the modifier gas may be a gas that is not ordinarily present in blood or serum. However, the modifier gas must be capable of diluting and maintaining the gas osmotic agent or agents at a partial pressure below the vapor pressure of the gas osmotic agent or agents while the gases in blood or other surrounding liquid diffuse into the bubble. In an aqueous medium, water vapor is not considered to be one of the "gases" in question. Similarly, when microbubbles are in a nonaqueous liquid medium, the vapor of that medium is not considered to be one of the "gases."

We have discovered that by adding a gas osmotic agent that has, for example, a reduced membrane permeability through the bubble's surface or reduced solubility in the external continuous phase liquid phase, the life of a bubble formed therewith will be radically increased. This stabilizing influence can be understood more readily through a discussion of certain theoretical bubbles. First, we will consider the effects of arterial pressure and surface tension on a hypothetical microbubble containing only air.

Initially, a hypothetical bubble containing only air is prepared. For purposes of discussion, this bubble will initially be considered to have no Laplace pressure. Generally, when equilibrated at standard temperature and pressure (STP), it will have a internal pressure of 760 Torr of air and the surrounding fluid air concentration will also be equilibrated at 760 Torr (i.e., the fluid has an air tension of 760 Torr). Such a bubble will neither shrink nor grow.

Next, when the above hypothetical bubble is introduced into the arterial system, the partial pressure of air (or air tension) in the blood (the air pressure at which the blood was saturated with air) will also be approximately 760 Torr and there will be an arterial pressure (for the purposes of the this discussion at 100 Torr). This total creates an external pressure on the bubble of 860 Torr, and causing the gases in the bubble to be compressed until the internal pressure increases to 860 Torr. There then arises a difference of 100 Torr between the air pressure inside the bubble and the air tension of the fluid surrounding the bubble. This pressure differential causes air to diffuse out of the bubble, through its airpermeable surface membrane, causing the bubble to shrink (i.e., lose air) as it strives to reach equilibrium. The bubble shrinks until it disappears.

Next, consider the additional, and more realistic, effect on the hypothetical bubble of adding the surface tension of the bubble. The surface tension of the bubble leads to a Laplace pressure exerted on gas inside the bubble. The total pressure exerted on the gas inside the bubble is computed through adding the sum of the atmospheric pressure, the arterial pressure and the Laplace pressure. In a 3 µm bubble a surface tension of 10 dynes per centimeter is attainable with well chosen surfactants. Thus, the Laplace pressure exerted on the hypothetical 3 µm bubble is approximately 100 Torr and, in addition, the arterial pressure of 100 Torr is also exerted on the bubble. Therefore, in our hypothetical bubble, the total external pressure applied to the gas inside the bubble is 960 Torr.

The bubble will be compressed until the pressure of the air inside the bubble rises to 960 Torr. Accordingly, a concentration differential of 200 Torr arises between the air inside the bubble and the air dissolved in the blood. Therefore, the bubble will rapidly shrink and disappear even more rapidly than it did in the previous case, as it attempts to reach equilibrium.

The discovery of the present invention is illustrated by considering a third hypothetical microbubble containing air and a gas osmotic agent or a secondary gas. Assume that a theoretical bubble, initially having no arterial pressure and no Laplace pressure, is prepared having a total pressure of 760 Torr, which is made up of air at a partial pressure of 684 Torr and a perfluorocarbon ("PFC") as a gas osmotic agent at a partial pressure of 76 Torr. Further, assume that the perfluorocarbon is selected to have one or more traits that make it capable of acting as an appropriate gas osmotic agent, such as limited bubble membrane permeability or limited solubility in the external liquid phase. There is an initial gas osmotic pressure differential between the 684 Torr of air within the bubble and the 760 Torr of air tension outside the bubble (assuming STP) of 76 Torr. This 76 Torr initial pressure difference is the initial gas osmotic pressure and will cause the bubble to expand. Air from outside of the bubble will diffuse into and inflate the bubble, driven by the osmotic pressure differential, similar to the way water diffuses into a dialysis bag containing a starch solution, and inflates the bag.

The maximum gas osmotic pressure this gas mixture can develop is related to the partial pressure of the PFC and the ratio of the permeability of the PFC to the permeability of the air in the surrounding fluid. In theory, and as observed experimentally, the bubble will grow indefinitely as the system attempts to reach osmotic equilibrium between the concentration of air (equivalent to the partial pressure of air) within the bubble and the concentration of air surrounding the bubble (the air tension).

When the hypothetical mixed gas bubble is exposed to 100 Torr of arterial pressure where the blood has a dissolved air tension of 760 Torr, the total external pressure will equal 860 Torr (760 Torr atmospheric pressure and 100 Torr arterial pressure). The bubble will compress under the arterial pressure, causing the internal pressure of the bubble to reach 860 Torr. The partial pressure of the air will increase to 774 Torr and the partial pressure of the PFC (the second gas) will increase to 86 Torr. The air will diffuse out of the bubble until it reaches osmotic equilibrium with the air dissolved in the blood (i.e., 760 Torr) and the partial pressure of the PFC will increase to 100 Torr. The partial pressure of the PFC will act to counterbalance the pressure exerted due to the arterial pressure, halting shrinkage of the bubble, in each case, assuming that the permeability of the bubble to the PFC is negligible.

When the surface tension or Laplace pressure component of 100 Torr is added (as discussed above with the air bubble), a total of 200 Torr additional pressure is exerted on the gas in the bubble. Again, the bubble will compress until and the pressure inside the bubble increases to 960 Torr (partial pressure of air 864 and partial pressure of PFC 96). The air will diffuse from the bubble until it reaches 760 Torr (in equilibrium with the concentration of air dissolved in the blood) and the partial pressure of the PFC will increase to 200 Torr, where, again, the gas osmotic pressure induced by the PFC will act to counterbalance the pressure exerted by the Laplace pressure and the arterial pressure, again, assuming that the membrane permeability of the bubble to the PFC is negligible.

Similarly, if the partial pressure of air in the bubble is lower than the air tension in the surrounding liquid, the bubble will actually grow until the PFC is sufficiently diluted by incoming air so that the pressure of air inside and the air tension outside of the bubble are identical.

Thus, bubbles can be stabilized effectively through the use of combinations of gases, since the correct combination of gases will result in a gas osmotic pressure differential that can be harnessed to counterbalance the effects of the Laplace pressure and the arterial pressure exerted on the a gas within the bubble in circulating blood.

Examples of particular uses of the microbubbles of the present invention include perfusion imaging of the heart, the myocardial tissue, and determination of perfusion characteristics of the heart and its tissues during stress or exercise tests, or perfusion defects or changes due to myocardial infarction. Similarly, myocardial tissue can be viewed after oral or venous administration of drugs designed to increase the blood flow to a tissue. Also, visualization of changes in myocardial tissue due to or during various interventions, such as coronary tissue vein grafting, coronary angioplasty, or use of thrombolytic agents (TPA or streptokinase) can also be enhanced. As these contrast agents can be administered conveniently via a peripheral vein to enhance the visualization of the entire circulatory system, they will also aid in the diagnosis of general vascular pathologies and in the ability to monitor the viability of placental tissue ultrasonically.

It should, however, be emphasized that these principles have application beyond ultrasound imaging. Indeed, the present invention is sufficiently broad to encompass the use of gas osmotic pressure to stabilize bubbles for uses in any systems, including nonbiological applications.

In a preferred embodiment, the microbubbles of the present invention have a surfactant-based bubble membrane. However, the principles of the invention can be applied to stabilize microbubbles of virtually any type. Thus, mixed gases or vapors of the type described above can stabilize albumin based bubbles, polysaccharide based microbubbles, spray dried microsphere derived microbubbles, and the like. This result is achieved through the entrapment, within the chosen microbubble, of a combination of gases, preferably a primary modifier gas or mixture of gases that will dilute a gas osmotic agent to a partial pressure less than the gas osmotic agent's vapor pressure until the modifier gas will exchange with gases normally present in the external medium. The gas osmotic agent or agents are generally relatively hydrophobic and relatively bubble membrane impermeable and also further possess the ability to develop gas osmotic pressures greater than 50, 75, or 100 Torr. In one preferred embodiment, the gas vapor pressure of the gas osmotic agent is preferably less than about 760 Torr at 37° C., preferably less than about 750, 740, 730, 720, 710, or 700 Torr, and in some embodiments less than about 650, 600, 500, or 400 Torr. In preferred embodiments, the vapor pressure of the primary modifier gas is at least 660 Torr at 37° C. and the vapor pressure of the gas osmotic agent is at least 100 Torr at 37° C. For in vivo imaging mean bubble diameters between 1 and 10 µm are preferred, with 3 to 5 µm most preferred. The invention may in one embodiment also be described as a mixture of a first gas or gases and a second gas or gases within generally spherical membranes to form microbubbles, where the first gas and the second gas are respectively present in a molar ratio of about 1:100, 1:75, 1:50, 1:30, 1:20, or 1:10 to about 1000:1, 500:1, 250:1, 100:1, 75:1 or 50:1, and where the first gas has a vapor pressure of at least about (760−x) mm Hg at 37° C., where x is the vapor pressure of the second gas at 37° C., and where the vapor pressure of each of the first and second gases is greater than about 75 or 100 mm Hg at 37° C.

Microbubbles prepared in accordance with one preferred embodiment of the invention may also possess an additional advantageous property. In one such embodiment, mixtures of nonosmotic gases with osmotic stabilizing gases (or gas osmotic agents) are used to stabilize the resultant bubble size distribution during and immediately after production. Upon generation of the bubbles, the higher Laplace pressure in smaller bubbles causes diffusion through the liquid phase to the lower Laplace pressure larger bubbles. This causes the mean size distribution to increase above the capillary dimension limit of 5 microns over time. This is called disproportionation. When a mixture of a nonosmotic gas (e.g., air) is used with an osmotic vapor (e.g., $C_6F_{14}$) a slight reduction in volume of the smaller bubbles, due to air leaving the bubble, concentrates the osmotic gas and increases its osmotic pressure thus retarding further shrinkage while the larger bubbles increase in volume slightly, diluting the osmotic gas and retarding further growth.

An additional advantage of using a mixture of an extremely blood soluble gases (e.g., 87.5% by volume $CO_2$) and an osmotic gas mixture (e.g., 28% $C_6F_{14}$ vapor+72% air) is that, when injected, these bubbles rapidly shrink due to the loss of $CO_2$ to the blood. The bubbles, upon injection, will experience an 87.5% volume decrease due to loss of $CO_2$. This loss of $CO_2$ corresponds to a halving of the bubble diameter. Accordingly, one can prepare larger diameter bubbles (e.g., 9 µm), using simplified mechanical means, that will shrink to below 5 microns upon injection. In general, such bubbles will initially be prepared where the first gas is present in a ratio of at least 1:1 with respect to the second gas, preferably at least 3:2, 2:1, 3:1, 4:1, 5:1, or 10:1. Where the microbubble membrane is more permeable to the first gas than to the second gas (e.g., the membrane has respective permeabilities to the gases in a ratio of at least about 2:1, 3:1, 4:1, 5:1, or 10:1, preferably even higher, e.g., 20:1, 40:1, or 100:1), the bubbles advantageously shrink from their original first diameter to an average second diameter of 75% or less of their original diameter quite rapidly (e.g., within one, two, four, or five minutes). Then, when at least one relatively membrane-permeable gas is present in the aqueous medium surrounding the microbubble, the bubble is preferably stabilized at or about the second diameter for at least about 1 minute, preferably for 2, 3, 4, or 5 minutes. In one preferred embodiment, the bubbles maintain a size between about 5 or 6 µm and 1 µm for at least 1, 2, 3, 4, or 5 minutes, stabilized by a gas osmotic pressure differential. The gas tension in the external liquid is preferably at least about 700 mm Hg. Moreover, a relatively membrane impermeable gas is also in the microbubble to create such an osmotic pressure differential.

I. MICROBUBBLE CONSTRUCTION

A. The Membrane-Forming Liquid Phase

The external, continuous liquid phase in which the bubble resides typically includes a surfactant or foaming agent.

Surfactants suitable for use in the present invention include any compound or composition that aids in the formation and maintenance of the bubble membrane by forming a layer at the interface between the phases. The foaming agent or surfactant may comprise a single compound or any combination of compounds, such as in the case of co-surfactants.

Examples of suitable surfactants or foaming agents include: block copolymers of polyoxypropylene polyoxyethylene, sugar esters, fatty alcohols, aliphatic amine oxides, hyaluronic acid aliphatic esters, hyaluronic acid aliphatic ester salts, dodecyl poly(ethyleneoxy)ethanol, nonylphenoxy poly(ethyleneoxy)ethanol, derivatized starches, hydroxy ethyl starch fatty acid esters, commercial food vegetable starches, dextrans, dextran fatty acid esters, sorbitol, sorbitol fatty acid esters, gelatin, serum albumins, and combinations thereof. Particularly preferred sugar esters are those with a component having a hydrophilic-lipophilic balance (HLB) of less than 8 including mono-, di-, tri- or polyesterified sucrose, trehalose, dextrose and fructose to produce stearate, behenate, palmitate, myristate, laurate and caproate (e.g. sucrose tristearate), as these sugar esters prolong microbubble stability. Other sugar esters contemplated for use in the present invention include those esterified with unsaturated fatty acids to form oleate, ricinoleate, linoleate, arachidate, palmitoleate and myristoleate. The HLB is a number between 0 and 40 assigned to emulsifying agents and substances which are emulsified. The HLB is indicative of emulsification behavior and is related to the balance between the hydrophilic and lipophilic portions of the molecule (Rosen, M., (1989), Surfactants and Interfacial Phenomena, Second Edition, John Wiley & Sons, New York, pp. 326–329).

In the present invention, preferred surfactants or foaming agents are selected from the group consisting of phospholipids, nonionic surfactants, neutral or anionic surfactants, fluorinated surfactants, which can be neutral or anionic, and combinations of such emulsifying or foaming agents.

The nonionic surfactants suitable for use in the present invention include polyoxyethylene-polyoxypropylene copolymers. An example of such class of compounds is Pluronic, such as Pluronic F-68. Also contemplated are polyoxyethylene fatty acids esters, such as polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof, and cholesterol. In addition, nonionic alkylglucosides such as Tweens®, Spans® and Brijs® having a component with an HLB less than 8 are also within the scope of the present invention. The Spans include sorbitan tetraoleate, sorbitan tetrastearate, sorbitan tristearate, sorbitan tripalmitate, sorbitan trioleate, and sorbitan distearate. Tweens include polyoxyethylene sorbitan tristearate, polyoxyethylene sorbitan tripalmitate, polyoxyethylene sorbitan trioleate. The Brij family is another useful category of materials, which includes polyoxyethylene 10 stearyl ether. Anionic surfactants, particularly fatty acids (or their salts) having 12 to 24 carbon atoms, may also be used. One example of a suitable anionic surfactant is oleic acid, or its salt, sodium oleate.

It will be appreciated that a wide range of surfactants can be used. Indeed, virtually any surfactant or foaming agent (including those still to be developed) capable of facilitating formation of the microbubbles can be used in the present invention. The optimum surfactant or foaming agent or combination thereof for a given application can be determined through empirical studies that do not require undue experimentation. Consequently, one practicing the art of the present invention should choose the surfactant or foaming agents or combination thereof based upon such properties as biocompatibility or their non-Newtonian behavior.

The blood persistence of a contrast agent is inversely proportional to the Laplace pressure which is proportional to the surface tension of the bubble. Reduced surface tension, therefore, increases blood persistence. Surfactants that form ordered structures (multilaminar sheets and rods) in solution and produce non-Newtonian viscoelastic surface tensions are especially useful. Such surfactants include many of the sugar based surfactants and protein or glycoprotein surfactants (including bovine, human, or other lung surfactants). One preferred type of such surfactant has a sugar or other carbohydrate head group, and a hydrocarbon or fluorocarbon tail group. A large number of sugars are known that can function as head groups, including glucose, sucrose, mannose, lactose, fructose, dextrose, aldose, and the like. The tail group preferably has from about 2 or 4 to 20 or 24 carbon atoms, and may be, for example, a fatty acid group (branched or unbranched, saturated or unsaturated) covalently bound to the sugar through an ester bond. The surface tension of bubbles produced with these surfactants greatly decreases as the surface is compressed by shrinkage of the bubble (e.g., when the bubble shrinks), and it is increased as the surface area of the bubble is increased (e.g., when the bubble grows). This effect retards disproportionation, which leads to narrower size distribution and longer persisting bubbles in the vial and in vivo. A preferred surfactant mixture that has the properties associated with non-Newtonian viscoelasticity includes a nonionic surfactant or other foaming surfactant in combination with one of the non-Newtonian viscoelastic surfactant such as one of the sugar esters (e.g. 2% Pluronic F-68 plus 1% sucrose stearate). Often the ratio of the nonionic surfactant to the non-Newtonian surfactant is from about 5:1 to about 1:5, with the surfactants together (whether non-Newtonian or more conventional) comprising 0.5 to 8%, more preferably about 1 to 5% (w/v) of the microbubble-forming liquid mixture.

The lowering of surface tension in small bubbles, counter to typical Laplace pressure, allows the use of more efficient gas osmotic agents such as higher molecular weight perfluorocarbons as the gas osmotic agent. With conventional surfactants, the higher molecular weight PFCs will condense at the high bubble pressures. Without these efficient surfactants higher boiling less membrane permeable PFCs, e.g. $C_6F_{14}$, would be extremely difficult.

One may also incorporate other agents within the aqueous phase. Such agents may advantageously include conventional viscosity modifiers, buffers such as phosphate buffers or other conventional biocompatible buffers or pH adjusting agents such as acids or bases, osmotic agents (to provide isotonicity, hyperosmolarity, or hyposmolarity). Preferred solutions have a pH of about 7 and are isotonic. However, when $CO_2$ is used as a first gas in a bubble designed to shrink rapidly to a first size, a basic pH can facilitate rapid shrinkage by removing $CO_2$ as it leaves the bubble, preventing a buildup of dissolved $CO_2$ in the aqueous phase.

B. The Gas Phase

A major aspect of the present invention is in the selection of the gas phase. As was discussed above, the invention relies on the use of combinations of gases to harness or cause differentials in partial pressures and to generate gas osmotic pressures, which stabilize the bubbles. The primary modifier gas is preferably air or a gas present in air. Air and/or fractions thereof are also present in normal blood and serum. Where the microbubbles are to be used in an environment different from blood, the primary modifier gas is preferably selected from gases normally present in the external medium. Another criteria is the ease with which the primary modifier gas is diffused into or out of the bubbles. Typically, air and/or fractions thereof are also readily permeable through conventional flexible or rigid bubble surfaces. These criteria, in combination, allow for the rapid diffusion of the primary modifier gas into or out of the bubbles, as required.

Modifier gases not present in the external medium can also be used. However, in this case the bubble will initially grow or shrink (depending on the relative permeability and concentrations of the external gases to the modifier) as the external gases replace the original modifier gas. If, during this process, the gas osmotic agent has not condensed, the bubble will remain stable.

The gas osmotic agent is preferably a gas that is less permeable through the bubble's surface than the modifier. It is also preferable that the gas osmotic agent is less soluble in blood and serum. Therefore, it will now be understood that the gas osmotic agent can be a gas at room or body temperature or it can ordinarily be a liquid at body temperature, so long as it has a sufficient partial or vapor pressure at the temperature of use to provide the desired osmotic effect.

Accordingly, fluorocarbons or other compounds that are not gases at room or body temperature can be used, provided that they have sufficient vapor pressure, preferably at least about 50 or 100 Torr at body temperature, or more preferably at least about 150 or 200 Torr. It should be noted that where the gas osmotic agent is a mixture of gases, the relevant measure of vapor pressure is the vapor pressure of the mixture, not necessarily the vapor pressure of the individual components of the mixed gas osmotic agent.

It is also important that where a perfluorocarbon is used as the osmotic agent within a bubble, the particular perfluorocarbon does not condense at the partial pressure present in the bubble and at body temperature. Depending on the relative concentrations of the primary modifier gas and the gas osmotic agent, the primary modifier gas may rapidly leave the bubble causing it to shrink and concentrate the secondary gas osmotic agent. Such shrinking may occur until the gas osmotic pressure equals the external pressure on the bubble (maximum absolute arterial pressure) plus the Laplace pressure of the bubble minus the air tension, or air saturation tension, of the blood (essentially one atmosphere). Thus the condensing partial pressure of the resulting gas mixture at 37° C. must be above the equilibrium partial pressure, discussed above, of the osmotic agent.

Representative fluorocarbons meeting these criteria and in increasing ability to stabilize microbubbles are as follows:

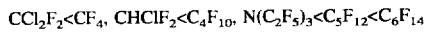

$CCl_2F_2 < CF_4, CHClF_2 < C_4F_{10}, N(C_2F_5)_3 < C_5F_{12} < C_6F_{14}$

Accordingly, it will be understood that PFC's with eight carbons atoms or fewer (37° C. vapor pressures greater than 80 mm Hg) are preferred. As will also be understood, however, it is possible to construct larger molecules with increased volatility through the addition of heteroatoms and the like. Therefore, the determination of the optimal secondary gas osmotic agent or gases agents is not size limited, but, rather, is based upon its ability to retain its vapor phase at body temperature and while providing a gas osmotic pressure equal to at least the sum of the arterial and Laplace pressures.

A listing of some compounds possessing suitable solubility and vapor pressure criteria is provided in Table I:

TABLE I perfluoro propanes, $C_3F_8$
perfluoro butanes, $C_4F_{10}$
perfluoro cyclo butanes, $C_4F_8$
perfluoro pentanes, $C_5F_{12}$
perfluoro cyclo pentanes, $C_5F_{10}$
perfluoro methylcyclobutanes, $C_5F_{10}$
perfluoro hexanes, $C_6F_{14}$
perfluoro cyclohexanes, $C_6F_{12}$
perfluoro methyl cyclopentanes, $C_6F_{12}$
perfluoro dimethyl cyclobutanes, $C_6F_{12}$
perfluoro heptanes, $C_7F_{16}$
perfluoro cycloheptanes, $C_7F_{14}$
perfluoro methyl cyclohexanes, $C_7F_{14}$
perfluoro dimethyl cyclopentanes, $C_7F_{14}$
perfluoro trimethyl cyclobutanes, $C_7F_{14}$
perfluoro triethylamines, $N(C_2F_5)_5$ It will be appreciated that one of ordinary skill in the art can readily determine other compounds that would perform suitably in the present invention that do not meet both the solubility and vapor pressure criteria, described above. Rather, it will be understood that certain compounds can be considered outside the preferred range in either solubility or vapor pressure, if such compounds compensate for the aberration in the other category and provide a superior insolubility or low vapor pressure.

It should also be noted that for medical uses the gases, both the modifier gas and the gas osmotic agent, should be biocompatible or not be physiologically deleterious. Ultimately, the microbubbles containing the gas phase will decay and the gas phase will be released into the blood either as a dissolved gas or as submicron droplets of the condensed liquid. It will be understood that gases will primarily be removed from the body through lung respiration or through a combination of respiration and other metabolic pathways in the reticuloendothelial system.

Appropriate gas combinations of the primary modifier and secondary gases can be ascertained empirically without undue experimentation. Such empirical determinations are described in the Examples.

When an efficient surfactant, e.g., bovine lung surfactant, is employed to produce a large diameter bubble with a low surface tension, the Laplace pressure is very low. When perfluorooctylbromide (PFOB) saturated air is inside the bubble and the bubble is exposed to air or a liquid nearly saturated with air (e.g., equilibrated with air) the gas osmotic pressure is greater than the Laplace pressure and therefore the bubble grows. With smaller diameter bubbles the Laplace pressure is higher and therefore the bubble shrinks and collapses. This shrinkage is at a reduced rate being driven by the difference between the Laplace pressure and the gas osmotic pressure. When small diameter bubbles are created by sonicating gas or gas vapor mixtures in a low surface tension surfactant solution, e.g., 2% pluronic F-68 plus 1% sucrose stearate, the time the bubbles persist in vitro, as observed by microscope, and in vivo as observed by Doppler ultrasound imaging of a rabbit's kidney post intravenous injection, correlated with the above gas osmotic pressure comparison.

In the rabbit kidney Doppler experiment (Example III), contrast enhancement was observed for up to 10 minutes with perfluorohexane/air mixtures in the bubbles compared with the instantaneous disappearance of contrast with pure air microbubbles. Thus, these perfluorochemicals are capable of exerting gas osmotic pressures that nearly counterbalance the Laplace pressure and create functional ultrasound microbubble contrast agents.

A surprising discovery was that mixtures of PFCs, e.g., $C_4F_{10}$ (as a combination modifier gas and a gas osmotic agent) saturated with $C_6F_{14}$ vapor (as the main gas osmotic agent), can stabilize the bubble for longer times than either component alone. This is because $C_4F_{10}$ is a gas at body temperature (and, thus, can act as both a modifier gas and a gas osmotic agent) has a somewhat reduced membrane permeability and it is only slightly soluble in $C_6F_{14}$ at body temperature. In this situation the gas osmotic pressures of both agents are added together, leading to increased bubble persistence over that of air/$C_6F_{14}$ only mixtures. It is possible that the condensing point of the longer persisting higher molecular weight $C_6F_{14}$ component is increased, allowing a larger maximum gas osmotic pressure to be exerted. Other mixtures of PFCs will perform similarly. Preferred mixtures of PFCs will have ratios of 1:10 to 10:1, and include such mixtures as perfluorobutane/perfluorohexane and perfluorobutane/perfluoropentane. These preferred fluorochemicals can be branched or straight chain.

As was discussed above, we have also discovered that mixtures of nonosmotic gases in combination with the gas osmotic agent act to stabilize the size distribution of the bubbles before and after injection. Upon generation of the bubbles, the higher Laplace pressures in smaller bubbles causes diffusion through the liquid phase to the lower Laplace pressure larger bubbles. This causes the mean size distribution to increase above the capillary dimension limit of 5 microns with time. This is called disproportionation.

However, when a mixture of a modifier gases (e.g., air or carbon dioxide) are used with a gas osmotic agent (e.g., $C_6F_{14}$) a slight reduction in volume of the smaller bubbles, due to one of the modifier gases leaving the bubble, will concentrate the osmotic gas and increases its osmotic pressure, thus, retarding further shrinkage. On the other hand, the larger bubbles will increase in volume slightly, diluting the osmotic gas and also retarding further growth.

An additional advantage of using a mixture of an extremely blood soluble gas (e.g., 75% through 87.5% by volume $CO_2$) and an osmotic gas mixture (e.g. 28% $C_6F_{14}$ vapor and 72% air) is that when injected, these bubbles rapidly shrink due to the loss of $CO_2$ to the blood. Carbon dioxide leaves particularly fast due to a specific plasma enzyme that catalyzes its dissolution. An 87.5% volume decrease due to loss of $CO_2$ corresponds with a halving of the bubble diameter. Accordingly, larger diameter bubbles can be produced which will shrink to an appropriate size (i.e., 5 microns) upon injection or exposure to a solution with a basic or alkaline pH.

Accordingly, we have discovered that through use of a gas that is relatively hydrophobic and that has a relatively low membrane permeability, the rate of contrast particle decay can be reduced. Thus, through reducing the particle decay rate, the microbubbles' half lives are increased and contrast enhancement potential is extended.

II. OTHER COMPONENTS

It will be understood that other components can be included in the microbubble formulations of the present invention. For example, osmotic agents, stabilizers, chelators, buffers, viscosity modulators, air solubility modifiers, salts, and sugars can be added to fine tune the microbubble suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation.

III. FORMATION OF THE MICROBUBBLES OF THE PRESENT INVENTION

There are a variety of methods to prepare microbubbles in accordance with the present invention. Sonication is preferred for the formation of microbubbles, i.e., through an ultrasound transmitting septum or by penetrating a septum with an ultrasound probe including an ultrasonically vibrating hypodermic needle. However, it will be appreciated that a variety of other techniques exist for bubble formation. For example, gas injection techniques can be used, such as venturi gas injection.

Other methods for forming microbubbles include formation of particulate microspheres through the ultrasonication of albumin or other protein as described in European Patent Application 0,359,246 by Molecular Biosystems, Inc.; the use of tensides and viscosity increasing agents as described in U.S. Pat. No. 4,446,442; lipid coated, non-liposomal, microbubbles as is described in U.S. Pat. No. 4,684,479; liposomes having entrapped gases as is described in U.S. Pat. Nos. 5,088,499 and 5,123,414; and the use of denatured albumin particulate microspheres as is described in U.S. Pat. No. 4,718,433. The disclosure of each of the foregoing patents and applications is hereby incorporated by reference.

Any of the above methods can be employed with similar success to entrain the modifier gases and gas osmotic agents of the present invention. Moreover, it is expected that similar enhancement in longevity of the bubbles created will be observed through use of the invention.

Sonication can be accomplished in a number of ways. For example, a vial containing a surfactant solution and gas in the headspace of the vial can be sonicated through a thin membrane. Preferably, the membrane is less than about 0.5 or 0.4 mm thick, and more preferably less than about 0.3 or even 0.2 mm thick, i.e., thinner than the wavelength of ultrasound in the material, in order to provide acceptable transmission and minimize membrane heating. The membrane can be made of materials such as rubber, Teflon, Mylar, urethane, aluminized film, or any other sonically transparent synthetic or natural polymer film or film forming material. The sonication can be done by contacting or even depressing the membrane with an ultrasonic probe or with a focused ultrasound "beam." The ultrasonic probe can be disposable. In either event, the probe can be placed against or inserted through the membrane and into the liquid. Once the sonication is accomplished, the microbubble solution can be withdrawn from and vial and delivered to the patient.

Sonication can also be done within a syringe with a low power ultrasonically vibrated aspirating assembly on the syringe, similar to an inkjet printer. Also, a syringe or vial may be placed in and sonicated within a low power ultrasonic bath that focuses its energy at a point within the container.

Other types of mechanical formation of microbubbles are also contemplated. For example, bubbles can be formed with a mechanical high shear valve (or double syringe needle) and two syringes, or an aspirator assembly on a syringe.

Even simple shaking may be used. The shrinking bubble techniques described herein are particularly suitable for mechanically formed bubbles, having lower energy input than sonicated bubbles. Such bubbles will typically have a diameter much larger than the ultimately desired biocompatible imaging agent, but can be made to shrink to an appropriate size in accordance with the present invention.

In another method, microbubbles can be formed through the use of a liquid osmotic agent emulsion supersaturated with a modifier gas at elevated pressure introduced into in a surfactant solution. This production method works similarly to the opening of soda pop, where the gas foams upon release of pressure forming the bubbles.

In another method, bubbles can be formed similar to the foaming of shaving cream, where perfluorobutane, freon, or another like material that boils when pressure is released. However, in this method it is imperative that the emulsified liquid boils at sufficiently low temperatures or that it contain numerous bubble nucleation sites so as to prevent superheating and supersaturation of the aqueous phase. This supersaturation will lead to the generation of a small number of large bubbles on a limited number of nucleation sites rather than the desired large number of small bubbles (one for each droplet).

In still another method, dry void-containing particles or other structures (such as hollow spheres or honeycombs) that rapidly dissolve or hydrate, preferably in an aqueous solution, e.g., albumin, microfine sugar crystals, hollow spray dried sugar, salts, hollow surfactant spheres, dried porous polymer spheres, dried porous hyaluronic acid, or substituted hyaluronic acid spheres, or even commercially available dried lactose microspheres can be stabilized with a gas osmotic agent.

For example, a spray dried surfactant solution can be formulated by atomizing a surfactant solution into a heated gas such as air, carbon dioxide, nitrogen, or the like to obtain dried 1–10 micron or larger hollow or porous spheres, which are packaged in a vial filled with an osmotic gas or a desired gas mixture as described herein. The gas will diffuse into the voids of the spheres. Diffusion can be aided by pressure or vacuum cycling. When reconstituted with a sterile solution the spheres will rapidly dissolve and leave osmotic gas stabilized bubbles in the vial. In addition, the inclusion of starch or dextrins, a sugar polyester and/or an inflating agent such as methylene chloride, 1,1,2-trichlorotrifluoroethane (Freon® 113, EM Science, Gibbstown, N.J.) or perfluorohexane, will result in microbubbles with an increased in vivo half-life. Particularly preferred starches for use in formation of microbubbles include those with a molecular weight of greater than about 500,000 daltons or a dextrose equivalency (DE) value of less than about 12. The DE value is a quantitative measurement of the degree of starch polymer hydrolysis. It is a measure of reducing power compared to a dextrose standard of 100. The higher the DE value, the greater the extent of starch hydrolysis. Such preferred starches include food grade vegetable starches of the type commercially available in the food industry, including those sold under the trademarks N-LOK and CAPSULE by National Starch and Chemical Co., (Bridgewater, N.J.); derivatized starches, such as hydroxyethyl starch (available under the trademarks HETASTARCH and HESPAN from du Pont Pharmaceuticals) (M-Hydroxyethylstarch, Ajinimoto, Tokyo, Japan). (Note that short chain starches spray dry well and can be used to produce microbubbles, but are not preferred because those with a molecular weight less than about 500,000 do not stabilize the microbubbles. However, they can be used in the present invention in applications in which additional stabilization is not required.) In the alternative, a lyophilized cake of surfactant and bulking reagents produced with a fine pore structure can be placed in a vial with a sterile solution and a head spaced with an osmotic gas mixture. The solution can be frozen rapidly to produce a fine ice crystal structure and, therefore, upon lyophilization produces fine pores (voids where the ice crystals were removed).

Alternatively, any dissolvable or soluble void-forming structures may be used. In this embodiment, where the void-forming material is not made from or does not contain surfactant, both surfactant and liquid are supplied into the container with the structures and the desired gas or gases. Upon reconstitution these voids trap the osmotic gas and, with the dissolution of the solid cake, form microbubbles with the gas or gases in them.

Figure 2:
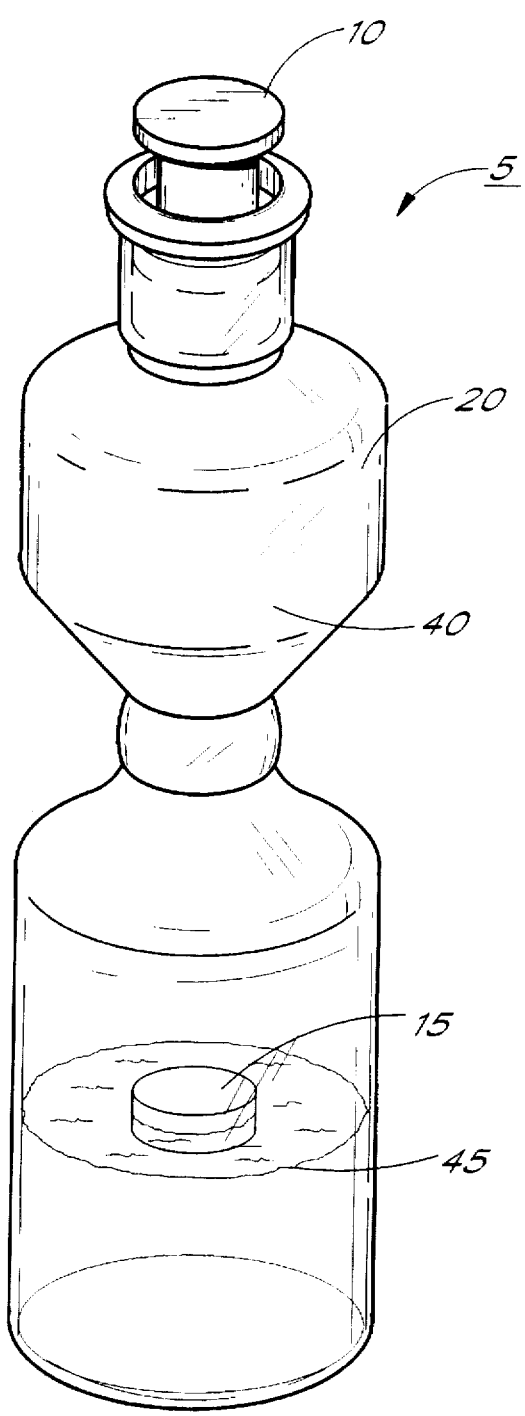
FIG. 2 illustrates the vial of FIG. 1, where the aqueous solution has been mixed with the solid ingredients to form microbubbles for administration to a patient.

It will be appreciated that kits can be prepared for use in making the microbubble preparations of the present invention. These kits can include a container enclosing the gas or gases described above for forming the microbubbles, the liquid, and the surfactant. The container can contain all of the sterile dry components, and the gas, in one chamber, with the sterile aqueous liquid in a second chamber of the same container. Suitable two-chamber vial containers are available, for example, under the trademarks WHEATON RS177FLW or S-1702FL from Wheaton Glass Co., (Millville, N.J.). Such a container is illustrated in FIGS. 1–4. Referring to FIGS. 1 and 2, the illustrated Wheaton container 5 has an upper chamber 20 which can contain an aqueous solution 25, and a lower chamber 30 which can contain the dried ingredients 35 and a desired gas. A stopper 10 is provided separating the top chamber from the environment, and a seal 15 separates the upper chamber 20 from the lower chamber 30 containing spray dried (powdered) hollow microsphere 35 and the gas osmotic agent. Depressing the stopper 10 pressurizes the relatively incompressible liquid, which pushes the seal 15 downward into the lower chamber 30. This releases aqueous solution 25 into lower chamber 30, resulting in the dissolution of powder 35 to form stabilized microbubbles 45 containing the entrapped gas osmotic agent. Excess gas osmotic agent 40 is released from the lower chamber 30 into the upper chamber 20. This arrangement is convenient for the user and has the added unexpected advantage of sealing the small quantity of water-impermeable gas osmotic agent in the lower chamber by covering the interchamber seal with a thick (0.5 to 1.25 inch) layer of aqueous solution and the advantage that the aqueous solution can be introduced into the lower chamber without raising the pressure in the powder chamber by more than about 10%. Thus, there is no need for a pressure vent. (In contrast, conventional reconstitution of a solute in a single chamber vial with a needle and syringe without a vent can result in the production of considerable intrachamber pressure which could collapse the microbubbles.) The formation of microbubbles by this method is described in Example XIII.

Figure 3:
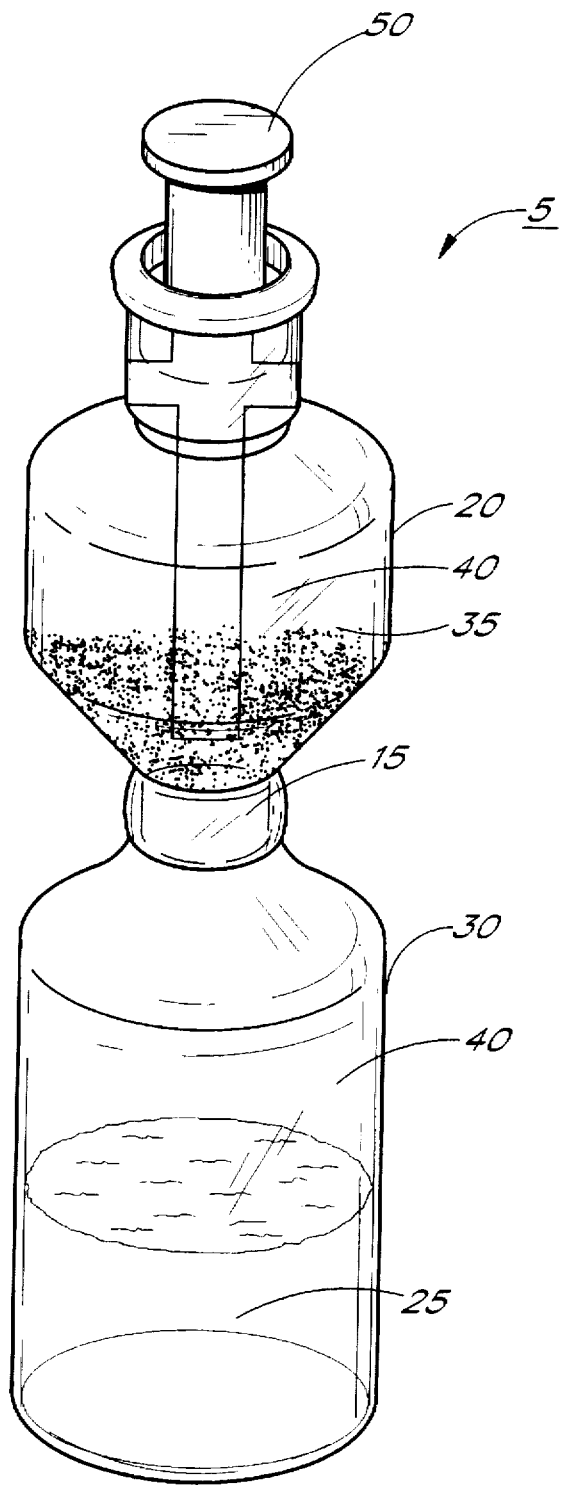
FIG. 3 is a perspective view of an inverted two-chamber vial containing a microbubble-forming preparation, with an aqueous solution in the lower chamber and solid and gaseous ingredients in the upper chamber.
Figure 4:
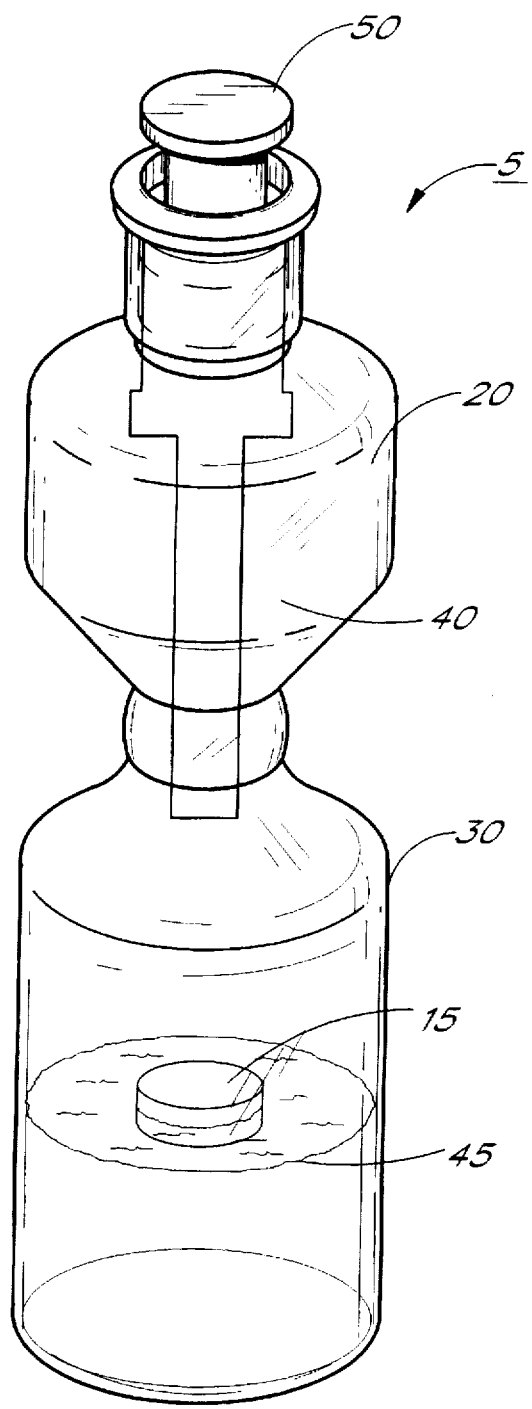
FIG. 4 illustrates the vial of FIG. 3, where the aqueous solution has been mixed with the solid ingredients to form microbubbles for administration to a patient.

Alternatively, an inverted two-chamber vial may be used for microbubble preparation. Referring to FIGS. 3 and 4, the same vial is used as described hereinabove, except that the stopper 50 is elongated such that it dislodges inner seal 15 when depressed. In this microbubble preparation method, the spray dried hollow microspheres 35 and the gas osmotic agent 40 are contained in the upper chamber 20. The aqueous solution 25 and gas osmotic agent 40 are contained within lower chamber 30. When stopper 50 is depressed, it dislodges seal 15 allowing the spray dried hollow microspheres to mix with the aqueous solution 25 in the presence of gas osmotic agent 40. One advantage associated with this method of microbubble formation is that the aqueous phase can be instilled first and sterilized via autoclaving or other means, followed by instillation of the spray dried microspheres. This will prevent potential microbial growth in the aqueous phase prior to sterilization.

Although one particular dual chamber container has been illustrated, other suitable devices are known and are commercially available. For example, a two compartment glass syringe such as the B-D HYPAK Liquid/Dry 5+5 ml Dual Chamber prefilled syringe system (Becton Dickinson, Franklin Lakes, N.J.; described in U.S. Pat. No. 4,613,326) can advantageously be used to reconstitute the spray dried powder. The advantages of this system include:

1. Convenience of use;
2. The aqueous-insoluble gas osmotic agent is sealed in by a chamber of aqueous solution on one side and an extremely small area of elastomer sealing the needle on the other side; and
3. a filtration needle such as Monoject #305 (Sherwood Medical, St. Louis, Mo.) can be fitted onto the syringe at the time of manufacture to ensure that no undissolved solids are injected.

The use of the two chamber syringe to form microbubbles is described in Example XIV.

It can be appreciated by one of ordinary skill in the art that other two-chamber reconstitution systems capable of combining the spray dried powder with the aqueous solution in a sterile manner are also within the scope of the present invention. In such systems, it is particularly advantageous if the aqueous phase can be interposed between the water-insoluble osmotic gas and the environment, to increase shelf life of the product.

Alternatively, the container can contain the void forming material and the gas or gases, and the surfactant and liquid can be added to form the microbubbles. In one embodiment, the surfactant can be present with the other materials in the container, so that only the liquid needs to be added in order to form the microbubbles. Where a material necessary for forming the microbubbles is not already present in the container, it can be packaged with the other components of the kit, preferably in a form or container adapted to facilitate ready combination with the other components of the kit.

The container used in the kit may be of the type described elsewhere herein. In one embodiment, the container is a conventional septum-sealed vial. In another, it has a means for directing or permitting application of sufficient bubble forming energy into the contents of the container. This means can comprise, for example, the thin web or sheet described previously.

Various embodiments of the present invention provide surprising advantages. The spray dried starch formulations give prolonged in-vial stability of the microbubbles, particularly when the molecular weight of the starch is over about 500,000. Use of fatty acid esters of sugars containing a component with an HLB of less than 8 provides greatly increased in vivo and in-vial stability. Fatty acid esters of sugars such as sucrose monosterate, as well as block copolymers such as Pluronic F-68 (with an HLB over 12) allow the powder to form bubbles at the instant they are rehydrated. Spray dried formulations with a structural agent such as a starch, starch derivative, or dextrin provide a significantly lower total dose of surfactant than comparable sonicated formulations. The use of two-chamber vials with water providing an additional seal for the fluorocarbon gas provide increased shelf life, and greater use convenience. Spray dried formulations with a structural agent (such as a starch or dextrin) and a sugar polyester provide microbubbles with greatly increased in vivo half lives.

The inclusion of an inflating agent in the solution to be spray-dried results in a greater ultrasound signal per gram of spray-dried powder by forming a greater number of hollow microspheres. The inflating agent nucleates steam bubble formulation within the atomized droplets of the solution entering the spray dryer as these droplets mix with the hot air stream within the dryer. Suitable inflating agents are those that supersaturate the solution within the atomized droplets with gas or vapor, at the elevated temperature of the drying droplets (approximately 100° C.). Suitable agents include:

1. Dissolved low-boiling (below 100° C.) solvents with limited miscibility with aqueous solutions, such as methylene chloride, acetone and carbon disulfide used to saturate the solution at room temperature.
2. A gas, e.g. $CO_2$ or $N_2$, used to saturate the solution at room temperature and elevated pressure (e.g. 3 bar). The droplets are then supersaturated with the gas at 1 atmosphere and 100° C.
3. Emulsions of immiscible low-boiling (below 100° C.) liquids such as Freon® 113, perfluoropentane, perfluorohexane, perfluorobutane, pentane, butane, FC-11 ($CCL_3F$), FC-11B1 ($CBrCl_2F$), FC-11B2 ($CBr_2ClF$), FC12B2 ($CF_2Br_2$), FC21 ($CHCl_2F$), FC21B1 (CHBrClF), FC-21B2 ($CHBr_2F$), FC-31B1 ($CH_2BrF$), FC113A ($CCl_3CF_3$), FC-122 ($CClF_2CHCl_2$), FC-123 ($CF_3CHCl_2$), FC-132 (CHClFCHClF), FC-133 ($CHClFCHF_2$), FC-141 ($CH_2ClCHClF$), FC-141B ($CCl_2FCH_3$), FC-142 ($CHF_2CH_2Cl$), FC-151 ($CH_2FCH_2Cl$), FC-152 ($CH_2FCH_2F$), FC-1112 (CClF=CClF), FC-1121 (CHCl=CFCl) and FC-1131 (CHCl=CHF)

The inflating agent is substantially evaporated during the spray drying process and thus is not present in the final spray-dried powder in more than trace quantities.

The inclusion of the surfactants and wetting agents into the shell of the microsphere allows the use of a lower surfactant concentration. As the microsphere shell is dissolving, it temporarily surrounds the microbubble formed in its interior with a layer of aqueous phase that is saturated with the surfactants, enhancing their deposition on the microbubble's surface. Thus, spray-dried surfactant containing microspheres require only locally high concentrations of surfactant, and obviate the need for a high surfactant concentration in the entire aqueous phase.

Any of the microbubble preparations of the present invention may be administered to a vertebrate, such as a bird or a mammal, as a contrast agent for ultrasonically imaging portions of the vertebrate. Preferably, the vertebrate is a human, and the portion that is imaged is the vasculature of the vertebrate. In this embodiment, a small quantity of microbubbles (e.g., 0.1 ml/Kg [2 mg/Kg spray-dried powder] based on the body weight of the vertebrate) is introduced intravascularly into the animal. Other quantities of microbubbles, such as from about 0.005 ml/Kg to about 1.0 ml/Kg, can also be used. Imaging of the heart, arteries, veins, and organs rich in blood, such as liver, lungs, and kidneys can be ultrasonically imaged with this technique.

The foregoing description will be more fully understood with reference to the following Examples. Such Examples, are, however, exemplary of preferred methods of practicing the present invention and are not limiting of the scope of the invention or the claims appended hereto.

EXAMPLE I

Preparation of Microbubbles Through Sonication

Microbubbles with an average number weighted size of 5 microns were prepared by sonication of an isotonic aqueous phase containing 2% Pluronic F-68 and 1% sucrose stearate as surfactants, air as a modifier gas and perfluorohexane as the gas osmotic agent.

In this experiment, 1.3 ml of a sterile water solution containing 0.9% NaCl, 2% Pluronic F-68 and 1% sucrose stearate was added to a 2.0 ml vial. The vial had a remaining head space of 0.7 ml initially containing air. Air saturated with perfluorohexane vapor (220 torr of perfluorohexane with 540 torr of air) at 25 degrees C. was used to flush the headspace of the vial. The vial was sealed with a thin 0.22 mm polytetrafluoroethylene (PTFE) septum. The vial was turned horizontally, and a ⅛" (3 mm) sonication probe attached to a 50 watt sonicator model VC50, available from Sonics & Materials was pressed gently against the septum. In this position, the septum separates the probe from the solution. Power was then applied to the probe and the solution was sonicated for 15 seconds, forming a white solution of finely divided microbubbles, having an average number weighted size of 5 microns as measured by Horiba LA-700 laser light scattering particle analyzer.

EXAMPLE II

Measurement of In-vitro Size of Microbubbles

The in-vitro size of the microbubbles prepared in Example I was measured by laser light scattering. Studies of bubbles were conducted where the microbubbles were diluted into a 4% dextrose water solution (1:50) circulating through a Horiba LA-700 laser light scattering analyzer. The average microbubbles size was 5 microns and doubled in size in 25 minutes.

Interestingly, microbubbles prepared through the same method in Example I without the use of a gas osmotic agent (substituting air for the perfluorohexane/air mixture) had an average size of 11 microns and gave only background readings on the particle analyzer at 10 seconds.

EXAMPLE III

Measurement of In-vivo Lifetime of Microbubbles

The lifetimes of microbubbles prepared in accordance with Example I were measured in rabbits through injecting 0.2 ml of freshly formed microbubbles into the marginal ear vein of a rabbit that was under observation with a Accuson 128XP/5 ultrasound imaging instrument with a 5 megahertz transducer. Several tests were conducted, during which images of the heart, inferior vena cava/aorta, and kidney were obtained while measuring the time and extent of the observable contrast enhancement. The results are presented in the following Table II:

TABLE II

| ORGAN | DOSE | TIME MAX. INTENSITY | TIME TO MINIMUM USABLE INTENSITY | TIME TO NO ENHANCE- MENT |
| --- | --- | --- | --- | --- |
| Heart | 0.1 ml/Kg | 7–10 sec. | 8–10 min. | 25 min. |
| IVC/Aorta | 0.1 ml/Kg | 7–10 sec. | 8–10 min. | 25 min. |
| Kidney | 0.1 ml/Kg | 7–10 sec. | 8–10 min. | 25 min. |

In Table III, a comparison of microbubbles prepared in an identical fashion without the use of an osmotic gas is presented (only air was used). Note that sporadic reflections were observed only in the right heart ventricle during the injection but disappeared immediately post dosing.

TABLE III

| ORGAN | DOSE | TIME TO MAXIMUM INTENSITY | TIME TO MINIMUM USABLE INTENSITY | TIME TO NO ENHANCE- MENT |
| --- | --- | --- | --- | --- |
| Heart | 0.1 ml/Kg | 0 | 0 | 0 |
| IVC/Aorta | 0.1 ml/Kg | 0 | 0 | 0 |
| Kidney | 0.1 ml/Kg | 0 | 0 | 0 |

The use of an osmotic agent dramatically increased the length of time for which microbubbles are visible.

EXAMPLE IV

Preparation of Mixed Osmotically Stabilized Microbubbles

Microbubbles with an average number weighted size of 5 microns were prepared by sonication of an isotonic aqueous phase containing 2% Pluronic F-68 and 1% sucrose stearate as surfactants and mixtures of perfluorohexane and perfluorobutane as the gas osmotic agents.

In this experiment, 1.3 ml of a sterile water solution containing 0.9% NaCl and 2% Pluronic F-68 was added to a 2.0 ml vial. The vial had a remaining head space of 0.7 ml, initially containing air. An osmotic gas mixture of perfluorohexane, 540 Torr and perfluorobutane at 220 Torr was used to flush the headspace before sealing with a thin 0.22 mm PTFE septum. The vial was sonicated as in Example I, forming a white solution of finely divided microbubbles, having an average particle size of 5 microns as measured by a Horiba LA-700 laser light scattering particle analyzer. This procedure was repeated twice more, once with pure perfluorobutane and then with a 540 Torr air+220 Torr perfluorohexane mixture. Vascular persistence of all three preparations was determined by ultrasound imaging of a rabbit post I.V. injection and are listed below

| 1.5 minutes | perfluorobutane |
| 2 minutes | perfluorohexane + air |
| 3 minutes | perfluorobutane + perfluorohexane |

The mixture of perfluorocarbons persisted longer than either agent alone.

EXAMPLE V

Preparation of Gas Osmotically Stabilized Microbubbles from Soluble Spray Dried Spheres Gas osmotically stabilized microbubbles were prepared by dissolving hollow spray dried lactose spheres, filled with an air perfluorohexane vapor mixture, in a surfactant solution.

Spray dried spheres of lactose with a mean diameter of approximately 100 micron and containing numerous 10 to 50 micron cavities, was obtained from DMV International under the trade name of PHARMATOSE DCL-11. Ninety milligrams of the lactose spheres was placed in a 2.0 ml vial. The porous spheres were filled with a mixture of 220 Torr perfluorohexane and 540 Torr air by cycling the gas pressure in the vial between one atmosphere and ½ atmosphere a total of 12 times over 5 minutes. A surfactant solution containing 0.9% sodium chloride, 2% Pluronic-F68 and 1% sucrose stearate was warmed to approximately 45° C., to speed the dissolution of the lactose, before injecting 1.5 ml of the warmed solution into the vial. The vial was then gently agitated by inversion for approximately 30 seconds to dissolve the lactose before injecting the microbubbles thus prepared into the Horiba LA-700 particle analyzer. A 7.7 micron volume weighted median diameter was measured approximately one minute after dissolution. The diameter of these microbubbles remained nearly constant, changing to a median diameter of 7.1 microns in 10 minutes. When the experiment was repeated with air filled lactose, the particle analyzer gave only background readings one minute after dissolution, thus demonstrating that gas osmotically stabilized microbubbles can be produced by the dissolution of gas-filled cavity-containing structures.

EXAMPLE VI

Preparation of Larger Bubbles That Shrink to a Desired Size

Microbubbles with an average volume weighted size of 20 microns shrinking to 2 microns were prepared by sonication of an isotonic aqueous phase containing 2% Pluronic F-68 as the surfactant, $CO_2$ as a diluent gas and perfluorohexane as the gas osmotic agent.

In this experiment, 1.3 ml of a sterile water solution containing 0.9% NaCl, 2% Pluronic F-68 and 1% sucrose stearate was added to a 2.0 ml vial. The vial had a remaining head space of 0.7 ml initially containing air. A mixture of air saturated with perfluorohexane at 25 degrees C. diluted by a factor of 10 with $CO_2$ (684 Torr $CO_2$+54 Torr air+22 Torr perfluorohexane) was used to flush the head space. The vial was sealed with a thin 0.22 mm PTFE septum. The vial was sonicated as in Example I, forming a white solution of finely divided microbubbles, having an average particle size of 28 microns as measured by Horiba LA-700 laser light scattering analyzer. In the 4% dextrose+0.25 mM NaOH solution of the Horiba, the average bubble diameter rapidly shrank in 2 to 4 minutes from 28 microns to 5 to 7 microns, and then remained relatively constant, reaching 2.6 micron after 27 minutes. This is because the $CO_2$ leaves the microbubbles by dissolving into the water phase.

EXAMPLE VII

Perfluoroheptane Stabilized Microbubble In vitro Experiment

Microbubbles were prepared as in Example I above employing perfluoroheptane saturated air (75 torr plus 685 torr air) and were measured as in Example II above. The average number weighted diameter of these microbubbles was 7.6 micron, one minute after circulation, and 2.2 microns after 8 minutes of circulation. This persistence, compared to the near immediate disappearance of microbubbles containing only air, demonstrates the gas osmotic stabilization of perfluoroheptane.

EXAMPLE VIII

Perfluorotripropyl Amine Stabilized Microbubble In vivo Experiment

Microbubbles were prepared as in Example I above, employing perfluorotripropyl amine saturated air and were assessed as in Example III above. The usable vascular persistence of these microbubbles was found to be 2.5 minutes, thus demonstrating the gas osmotic stabilization of perfluorotripropyl amine.

EXAMPLE IX

Effect of a Non Newtonian Viscoelastic Surfactant—Sucrose Stearate

Microbubbles were prepared as in Example I above employing 0.9% NaCl, 2% Pluronic F-68 and 2% sucrose stearate as the surfactant and with perfluoropropane saturated air and perfluorohexane saturated air in the headspace. These two preparations were repeated with the same surfactant solution minus sucrose stearate. All four microbubble preparations were assessed as in Example III above. The usable vascular persistence of these microbubbles are listed below:

2% Pluronic F-68+2% sucrose stearate persistence
  2 minutes perfluoropropane
  4 minutes perfluorohexane
2% Pluronic F-68 only persistence
  2 minutes perfluoropropane
  1 minute perfluorohexane As seen above, the reduced surface tension made possible by the non-Newtonian viscoelastic properties of sucrose stearate prevented the less volatile perfluorohexane from condensing, allowing perfluorohexane microbubbles of longer persistence to be produced.

EXAMPLE X

Spray Drying of Starch-containing Emulsion

One liter of each of the following solutions was prepared with water for injection: Solution A containing 4.0% w/v N-Lok vegetable starch (National Starch and Chemical Co., Bridgewater, N.J.) and 1.9% w/v sodium chloride (Mallinckrodt, St. Louis, Mo.) and Solution B containing 2.0% Superonic F-68 (Serra, Heidelberg, Germany) and 2.0% w/v Ryoto Sucrose Stearate S-1670 (Mitsubishi-Kasei Food Corp., Tokyo, Japan). Solution B was added to a high shear mixer and cooled in an ice bath. A coarse suspension of 40 ml 1,1,2-trichlorotrifluoroethane (Freon® 113; EM Science, Gibbstown, N.J.) was made in the 1 liter of solution B. This suspension was emulsified using a Microfluidizer (Microfluidics Corporation, Newton, Mass.; model M-110F) at 10,000 psi, 5° C. for 5 passes. The resulting emulsion was added to solution A to produce the following formula for spray drying:

2.0% w/v N-Lok
  1.0% w/v Superonic F-68
  1.0% w/v Sucrose Stearate S-1670
  0.95% w/v sodium chloride
  2.0% v/v 1,1,2-trichlorotrifluoroethane This emulsion was then spray dried in a Niro Atomizer Portable Spray Dryer equipped with a two fluid atomizer (Niro Atomizer, Copenhagen, Denmark) employing the following settings:

hot air flow rate=39.5 CFM
  inlet air temp.=235° C.
  outlet air temp.=10° C.
  atomizer air flow=110 liters/hr
  emulsion feed rate=1 liter/hr The dry, hollow spherical product had a diameter between about 1 µM and about 15 µM and was collected at the cyclone separator as is standard for this dryer. Aliquots of powder (250 mg) were weighed into 10 ml tubing vials, sparged with perfluorohexane-saturated nitrogen at 13° C. and sealed. The nitrogen was saturated with perfluorohexane by passing it through three perfluorohexane filled gas washing bottles immersed in a 13° C. water bath.

The vials were reconstituted with 5 ml water for injection after inserting an 18-gauge needle as a vent to relieve pressure as the water was injected. One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS. A peak signal of 1.6 volts RMS was observed with a half life of 52.4 seconds, thus demonstrating the ability of spray dried powders to produce intravascular echogenic microbubbles that have a prolonged half-life in vivo.

EXAMPLE XI

Production of Microbubbles Containing Hydroxyethyl Starch

An emulsion for spray drying was prepared as in Example X to give a final composition of:

2.0% w/v m-HES hydroxyethylstarch (Ajinimoto, Tokyo, Japan)

2.0% w/v sodium chloride (Mallinckrodt)

1.74% sodium phosphate, dibasic (Mallinckrodt)

0.26% w/v sodium phosphate, monobasic (Mallinckrodt)

1.7% w/v Superonic F-68 (Serva)

0.2% w/v Ryoto Sucrose Stearate S-1670 (Mitsubishi-Kasei Food Corp.)

0.1% w/v Ryoto Sucrose Stearate S-570 (Mitsubishi-Kasei Food Corp.)

4.0% w/v 1,1,2-trichlorotrifluoroethane (Freon® 113; EM Science, Gibbstown, N.J.)

This emulsion was spray dried as in Example X using the following parameters:

hot air flow rate=39.5 CFM inlet air temperature=220° C.

outlet air temperature=105° C.

atomizer air flow=110 liter/hr emulsion feed rate=1 liter/hr

Sample vials were prepared with 400 mg spray dried powder and sparged as in Example X. After reconstitution with 5 ml water for injection and intravenous administration of 1.0 ml to a rabbit as in Example X, a peak signal of 2.4 volts RMS was observed with a half life of 70.9 seconds. This demonstrates the ability of higher molecular weight and derivatized injectable grade starches and sugar polyesters to produce higher in vivo signals which persist longer as compared to standard vegetable starch (Example X). This also demonstrates the lower surfactant concentration required by an optimal spray dried formula and the use of a spray drying inflating agent such as Freon 113.

EXAMPLE XII

Stability of Starch-containing Microbubbles

The spray dried powder described in Example X was reconstituted as described. For comparison, the sonicated microbubbles from Example I were prepared and both were examined by light microscopy within 2 minutes of preparation and again at 10 minutes after preparation. The sonicated product was found to have a wider initial bubble diameter distribution (between about 1 and about 30 µM) than the reconstituted spray dried powder (between about 3 and about 15 µM). After 10 minutes, the vials were agitated, resampled and again observed by light microscopy. The reconstituted spray dried product was essentially unchanged, while the sonicated microbubbles had grown by disproportionation until nearly all of the observable microbubbles were more than 10 µM in diameter. This experiment demonstrates the extended in-vial stability of microbubbles produced by spray drying and the ability of starches to increase in vitro stability.

EXAMPLE XIII

Microbubble Formation Using Two Chamber Vial 800 mg spray dried powder from Example XII were weighed into the lower chamber of a 20 ml Wheaton RS-177FLW two chamber vial (FIG. 1). The vial was flushed with perfluorohexane-saturated nitrogen at 13° C. before inserting the interchamber seal. The upper chamber was filled with 10 ml sterile water for injection. The upper chamber stopper was inserted so as to eliminate all air bubbles in the upper chamber. Upon depression of the upper stopper, the interchamber seal was forced into the lower chamber, allowing the water to flow into the lower chamber and reconstitute the powder (FIG. 2). Numerous stable microbubbles were formed as demonstrated by light microscopy. This procedure demonstrates the convenience of this form of packaging and the elimination of the need to provide a vent to eliminate pressure buildup when the aqueous phase is added to the powder.

EXAMPLE XIV

Microbubble Formation Using Two Chamber Syringe

One hundred mg of the spray dried powder from Example XI was weighed into a 5 ml+5 ml HYPAK Liquid/Dry dual chamber syringe (Becton Dickinson, Franklin Lakes, N.J.) and shaken into the powder (needle end) chamber. The interchamber seal was then positioned just above the bypass channel. A 5 µM filter-containing needle was then fitted on the syringe. The powder-containing chamber was then filled with the gas osmotic agent by placing the assembly in a vacuum chamber, evacuating and refilling the chamber with the gas osmotic agent, perfluorohexane-saturated nitrogen at 13° C. The filter needle allows the evacuation and refilling of the atmosphere in the powder-containing chamber. A sealing needle cover was then placed on the needle. The liquid chamber was then filled with 4 ml water for injection and the plunger was seated using a temporary vent (wire inserted between the glass syringe barrel and the plunger so as to eliminate all air bubbles.

To reconstitute, the needle sealing cover was removed to eliminate pressure buildup in the powder chamber. The plunger was then depressed, forcing the interchamber seal to the bypass position which allowed the water to flow around the interchamber seal into the powder-containing chamber. The plunger motion was stopped when all the water was in the powder chamber. The syringe was agitated to dissolve the powder. Excess gas and any large bubbles were expelled by holding the syringe, needle end up, and further depressing the plunger. The solution containing numerous stabilized microbubbles (as observed by light microscopy) was then expelled from the syringe by depressing the plunger to its limit.

The foregoing description details certain preferred embodiments of the present invention and describes the best mode contemplated. It will be appreciated, however, that no matter how detailed the foregoing appears in text, the invention can be practiced in many ways and the invention should be construed in accordance with the appended claims and any equivalents thereof.

What is claimed is:

1. A method for forming microbubbles, comprising the steps of:

providing a first gas, a second component, a membrane forming material, and a liquid, wherein said first gas and said second component are present in a molar ratio of about 1:100 to about 1,000:1, and wherein said second component comprises vapor of a compound that is liquid at 37° C. and 760 mm Hg but which has a vapor pressure of at least 75 mm Hg at 37° C. with the proviso that said first gas and said second component are not water vapor; and surrounding said first gas and said second component with said membrane forming material to form microbubbles in said liquid.

2. The method of claim 1, wherein said membrane forming material is a surfactant.

3. The method of claim 2, wherein said membrane forming material comprises a non-Newtonian surfactant.

4. The method of claim 1, further comprising the steps of:

initially forming microbubbles having a first average diameter wherein the initial ratio of said first gas to said second component in said microbubbles is at least about 1:1;

contacting said microbubbles having a first average diameter with a liquid medium;

shrinking said microbubbles in said medium as a result of loss of said first gas through said membrane; and then stabilizing said microbubbles at a second average diameter of less than about 75% of said first diameter for a period of at least one minute.

5. The method of claim 4, wherein said microbubbles are stabilized at said second diameter by:

providing a gas osmotic pressure differential across said membrane such that the tension of a gas or gases dissolved in said medium is equal to or greater than the partial pressure of the same gas or gases inside said microbubbles.

6. The method of claim 5, wherein said first diameter is at least about 5 μm.

7. A method for forming microbubbles, comprising the steps of:

providing solid or semi-solid substantially liquid-soluble void-containing structures, said void-containing structures defining a plurality of voids having a diameter less than about 100 μm;

providing a halogenated gas in said voids;

providing a surfactant;

providing said void-containing structures, said halogenated gas, and said surfactant in admixture with a liquid in which said void-containing structures are soluble; and dissolving said void-containing structures in said liquid whereby the halogenated gas in said enclosures forms microbubbles that are surrounded by said surfactant.

8. The method of claim 7, wherein said void-containing structures are microspheres.

9. The method of claim 7, wherein said microbubbles contain a first gas and a second halogenated gas respectively present in a molar ratio of from about 1:100 to about 1000:1.

10. A method for imaging an object or body part or body cavity, comprising the steps of:

introducing into said object or body or body part or body cavity a microbubble preparation according to claim 1; and then imaging at least a portion of said body by ultrasound or magnetic resonance.

11. The method of claim 10, wherein said body is a vertebrate and said preparation is introduced into the vasculature or body cavity of said vertebrate.

12. The method of claim 10, wherein said preparation is a preparation as defined in claim 2.

13. The method of claim 10, wherein said preparation is a preparation as defined in claim 7.

14. The method of claim 10, wherein said preparation is a preparation as defined in claim 8.

15. The method of claim 10, further comprising the step of preparing said microbubble preparation prior to said introduction according to the method of claim 1.

16. The method of claim 10, further comprising the step of preparing said microbubble preparation prior to said introduction according to the method of claim 4.

17. The method of claim 10, further comprising the step of preparing said microbubble preparation prior to said introduction according to the method of claim 5.

18. The method of claim 10, further comprising the step of preparing said microbubble preparation prior to said introduction according to the method of claim 7.

19. A method for producing microbubbles having increased in-vial stability, comprising the steps of:

spray drying a liquid formulation containing a biocompatible film-forming material to form a microsphere powder therefrom;

combining the microspheres with a gas osmotic agent and storing the microspheres in a container with the gas osmotic agent; and then mixing an aqueous phase with the powder, wherein said powder substantially dissolves in the aqueous phase to form microbubbles.

20. The method of claim 19, wherein said film forming material comprises a starch or derivatized starch.

21. The method of claim 20, wherein said film forming material comprises a starch or derivatized starch having a molecular weight of greater than about 500,000 or a dextrose equivalency value less than about 12.

22. The method of claim 20, wherein said starch is hydroxyethyl starch.

23. The method of claim 19, wherein said film-forming material comprises a non-Newtonian surfactant.

24. The method of claim 19, wherein said gas osmotic agent comprises a fluorocarbon.

25. The method of claim 19, wherein said film forming material comprises a sugar ester.

26. The method of claim 25, wherein said sugar ester has a component with a hydrophilic-lipophilic balance less than about eight.

27. The method of claim 26, wherein said sugar ester component is sucrose tristearate.

28. A method for forming microbubbles, comprising the steps of:
providing a gas osmotic agent-permeated surfactant-containing powder; and
combining said powder with an aqueous phase.

29. A method for forming microbubbles, comprising the steps of:
providing a spray dried formulation comprising a starch, derivatized starch or dextrin;
providing a gas osmotic agent in combination with said spray dried formulation that permeates said formulation; and
combining said formulation with an aqueous phase to form microbubbles having a half-life in vivo of at least about 20 seconds.

30. The method of claim 29, wherein said spray dried formulation has been spray dried in combination with an inflating agent to form spray dried microspheres.

31. The method of claim 30, wherein said inflating agent is selected from the group consisting of: methylene chloride, Freon® 113, perfluorohexane and carbon dioxide.

32. The method of claim 29, wherein said spray dried formulation further comprises a sugar polyester.

33. The method of claim 1 wherein said second component comprises a gas osmotic agent.

34. The method of claim 33 wherein said gas osmotic agent comprises a fluorocarbon.

35. The method of claim 34 wherein said fluorocarbon is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

36. The method of claim 1 wherein said second component comprises perfluorohexane.

37. The method of claim 2 wherein said surfactant is selected from the group consisting of nonionic surfactants, neutral surfactants, anionic surfactants, neutral fluorinated surfactants, anionic fluorinated surfactants and combinations thereof.

38. The method of claim 1 wherein said membrane forming material is selected from the group consisting of phospholipids, block copolymers, sugar esters, fatty alcohols, aliphatic amine oxides, hyaluronic acid aliphatic esters, hyaluronic acid aliphatic ester salts, poly(ethyleneoxy)ethanol, nonylphenoxy poly(ethyleneoxy)ethanol, derivatized starches, hydroxy ethyl starch fatty acid esters, commercial food vegetable starches, dextrans, dextrin fatty acid esters, sorbitol, sorbitol fatty acid esters, gelatin, serum albumins and combinations thereof.

39. The method of claim 1, wherein said film-forming material comprises a protein.

40. The method of claim 1, wherein said film-forming material comprises a carbohydrate.

41. The method of claim 1 wherein said film-forming material comprises a compound selected from the group consisting of starches, derivatized starches and sugar esters.

42. The method of claim 7 wherein said halogenated gas comprises a fluorocarbon.

43. The method of claim 42 wherein said fluorocarbon is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

44. The method of claim 7 wherein said halogenated gas comprises perfluorohexane.

45. The method of claim 7, wherein said surfactant is a non-Newtonian surfactant.

46. The method of claim 7 wherein said surfactant is selected from the group consisting of nonionic surfactants, neutral surfactants, anionic surfactants, neutral fluorinated surfactants, anionic fluorinated surfactants and combinations thereof.

47. The method of claim 7 wherein said surfactant is selected from the group consisting of phospholipids, block copolymers, sugar esters, fatty alcohols, aliphatic amine oxides, hyaluronic acid aliphatic esters, hyaluronic acid aliphatic ester salts, poly(ethyleneoxy)ethanol, nonylphenoxy poly(ethyleneoxy)ethanol, derivatized starches, hydroxy ethyl starch fatty acid esters, commercial food vegetable starches, dextrans, dextrin fatty acid esters, sorbitol, sorbitol fatty acid esters, gelatin, serum albumins and combinations thereof.

48. The method of claim 7, wherein said void-containing structure comprises a powder.

49. The method of claim 7, wherein said void-containing structures comprise a carbohydrate.

50. The method of claim 7, wherein said void-containing structures comprise a compound selected from the group consisting of starch, derivatized starch, dextrin or combinations thereof.

51. The method of claim 7, wherein said void-containing structures comprise said surfactant.

52. The method of claim 51, wherein said surfactant is selected from the group consisting of phospholipids, fatty acids, block copolymers and sugar esters.

53. The method of claim 7, wherein said void containing structure comprises a protein.

54. The method of claim 24 wherein said fluorocarbon is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

55. The method of claim 19 wherein said gas osmotic agent comprises perfluorohexane.

56. The method of claim 19 wherein said film-forming material comprises a surfactant.

57. The method of claim 56 wherein said surfactant is selected from the group consisting of nonionic surfactants, neutral surfactants, anionic surfactants, neutral fluorinated surfactants, anionic fluorinated surfactants and combinations thereof.

58. The method of claim 56 wherein said surfactant is selected from the group consisting of phospholipids, block copolymers, sugar esters, fatty alcohols, aliphatic amine oxides, hyaluronic acid aliphatic esters, hyaluronic acid aliphatic ester salts, poly(ethyleneoxy)ethanol, nonylphenoxy poly(ethyleneoxy)ethanol, derivatized starches, hydroxy ethyl starch fatty acid esters, commercial food vegetable starches, dextrans, dextrin fatty acid esters, sorbitol, sorbitol fatty acid esters, gelatin, serum albumins and combinations thereof.

59. The method of claim 19, wherein said film-forming structures comprise a carbohydrate.

60. The method of claim 59 wherein said carbohydrate is selected from the group consisting of sugar crystals, spray dried sugar and dried lactose microspheres.

61. The method of claim 19, wherein said film-forming material comprises a protein.

62. The method of claim 28 wherein said gas osmotic agent-permeated surfactant-containing powder comprises a surfactant selected from the group consisting of nonionic surfactants, neutral surfactants, anionic surfactants, neutral fluorinated surfactants, anionic fluorinated surfactants and combinations thereof.

63. The method of claim 62 wherein said surfactant is selected from the group consisting of phospholipids, block copolymers, sugar esters, fatty alcohols, aliphatic amine oxides, hyaluronic acid aliphatic esters, hyaluronic acid aliphatic ester salts, poly(ethyleneoxy)ethanol, nonylphenoxy poly(ethyleneoxy)ethanol, derivatized starches, hydroxy ethyl starch fatty acid esters, commercial food vegetable starches, dextrans, dextrin fatty acid esters, sorbitol, sorbitol fatty acid esters, gelatin, serum albumins and combinations thereof.

64. The method of claim 28 wherein said surfactant-containing powder comprises a non-Newtonian surfactant.

65. The method of claim 28 wherein said non-Newtonian surfactant comprises one or more phospholipids.

66. The method of claim 28 wherein said gas osmotic agent-permeated surfactant-containing powder comprises a fluorocarbon.

67. The method of claim 66 wherein said fluorocarbon is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

68. The method of claim 28 wherein said gas osmotic agent comprises perfluorohexane.

69. The method of claim 28, wherein said gas osmotic agent-permeated surfactant-containing powder comprises a carbohydrate.

70. The method of claim 69 wherein said carbohydrate is selected from the group consisting of sugar crystals, spray dried sugar and dried lactose microspheres.

71. The method of claim 28, wherein said gas osmotic agent-permeated surfactant-containing powder comprises a protein.

72. The method of claim 28, wherein said gas osmotic agent-permeated surfactant-containing powder comprises a compound selected from the group consisting of starch, derivatized starch, dextrin or combinations thereof.

73. The method of claim 72, wherein said compound comprises a starch or derivatized starch having a molecular weight of greater than about 500,000 or a dextrose equivalency value less than about 12.

74. The method of claim 72, wherein said starch is hydroxyethyl starch.

75. The method of claim 29 wherein said spray dried formulation comprises a surfactant.

76. The method of claim 75 wherein said surfactant is selected from the group consisting of nonionic surfactants, neutral surfactants, anionic surfactants, neutral fluorinated surfactants, anionic fluorinated surfactants and combinations thereof.

77. The method of claim 75 wherein said surfactant is selected from the group consisting of phospholipids, block copolymers, sugar esters, fatty alcohols, aliphatic amine oxides, hyaluronic acid aliphatic esters, hyaluronic acid aliphatic ester salts, poly(ethyleneoxy)ethanol, nonylphenoxy poly(ethyleneoxy)ethanol, derivatized starches, hydroxy ethyl starch fatty acid esters, commercial food vegetable starches, dextrans, dextrin fatty acid esters, sorbitol, sorbitol fatty acid esters, gelatin, serum albumins and combinations thereof.

78. The method of claim 75 wherein said surfactant comprises a non-Newtonian surfactant.

79. The method of claim 78 wherein said non-Newtonian surfactant comprises one or more phospholipids.

80. The method of claim 29 wherein said gas osmotic agent comprises a fluorocarbon.

81. The method of claim 80 wherein said fluorocarbon is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

82. The method of claim 29 wherein said gas osmotic agent comprises perfluorohexane.

\* \* \* \* \*